(12) United States Patent
Seibel et al.

(10) Patent No.: US 10,852,291 B2
(45) Date of Patent: Dec. 1, 2020

(54) FLUIDIC DEVICE AND METHODS OF USE FOR PROCESSING TISSUE FOR PATHOLOGY

(71) Applicant: University of Washington, Seattle, WA (US)

(72) Inventors: Eric J. Seibel, Seattle, WA (US); Ronnie Das, Seattle, WA (US); Christopher W. Burfeind, Seattle, WA (US); Thu-mai Nguyen, Villejuif (FR)

(73) Assignee: University of Washington, Seattle, WA (US)

( * ) Notice: Subject to any disclaimer, the term of this patent is extended or adjusted under 35 U.S.C. 154(b) by 313 days.

(21) Appl. No.: 15/014,610

(22) Filed: Feb. 3, 2016

(65) Prior Publication Data

US 2016/0220990 A1 Aug. 4, 2016

Related U.S. Application Data

(60) Provisional application No. 62/111,236, filed on Feb. 3, 2015, provisional application No. 62/239,619, filed on Oct. 9, 2015.

(51) Int. Cl.
*G01N 33/483* (2006.01)
*G01N 21/59* (2006.01)
*B01L 3/00* (2006.01)

(52) U.S. Cl.
CPC .... *G01N 33/4833* (2013.01); *B01L 3/502715* (2013.01); *G01N 21/59* (2013.01);
(Continued)

(58) Field of Classification Search
CPC ....... B01L 2300/088; B01L 2300/0883; B01L 3/502715; B01L 2300/0867;
(Continued)

(56) References Cited

U.S. PATENT DOCUMENTS 6,773,567 B1  8/2004  Wolk
8,361,415 B2  1/2013  Di Carlo et al.
(Continued)

FOREIGN PATENT DOCUMENTS

DE  10251338 A1  6/2004
NO  2013111025 A1  8/2013
NO  2014070776 A1  5/2014

OTHER PUBLICATIONS

American Cancer Society, "Cancer Facts & Figures 2013," Atlanta: American Cancer Society, 64 pages, 2013.
(Continued)

*Primary Examiner* — Samuel P Siefke
(74) *Attorney, Agent, or Firm* — McDonnell Boehnen Hulbert & Berghoff LLP

(57) ABSTRACT

An example fluidic device may include a plurality of channels including one or more curved channels having a channel input and a channel output. Each of the one or more curved channels may have a substantially circular cross-section. The fluidic device may also include an input interface between the channel input of the one or more curved channels and an exterior of the fluidic device. The input interface may be configured to receive a biological tissue sample. The fluidic device may also include an output interface between the channel output of the one or more curved channels and the exterior of the fluidic device.

17 Claims, 14 Drawing Sheets

(52) U.S. Cl.
CPC .. *B01L 2200/0647* (2013.01); *B01L 2300/024* (2013.01); *B01L 2300/044* (2013.01); *B01L 2300/0627* (2013.01); *B01L 2300/088* (2013.01); *B01L 2300/0864* (2013.01); *B01L 2300/0867* (2013.01); *B01L 2300/0883* (2013.01); *B01L 2300/123* (2013.01); *B01L 2300/1827* (2013.01); *B01L 2400/0487* (2013.01)

(58) Field of Classification Search
CPC ....... B01L 2300/123; B01L 2200/0647; B01L 2300/1827; B01L 2300/0864; B01L 2300/044; B01L 2300/024; B01L 2400/0487; B01L 2300/0627; G01N 33/4833; G01N 21/59
See application file for complete search history.

(56) References Cited

U.S. PATENT DOCUMENTS

| | | | |
|---|---|---|---|
| 8,368,035 | B2 | 2/2013 | Seibel et al. |
| 2008/0003433 | A1* | 1/2008 | Mikami ............... B01J 19/0093 428/375 |
| 2008/0205739 | A1 | 8/2008 | Hayenga et al. |
| 2008/0223721 | A1* | 9/2008 | Cohen .................. B01L 3/5025 204/451 |
| 2009/0162853 | A1 | 6/2009 | Clark et al. |
| 2009/0170152 | A1 | 7/2009 | Reeser et al. |
| 2010/0081924 | A1 | 4/2010 | Hyde et al. |
| 2011/0096327 | A1* | 4/2011 | Papautsky .......... B01D 21/0087 356/335 |
| 2012/0145926 | A1* | 6/2012 | Seibel ................. G01N 21/4795 250/459.1 |
| 2012/0196320 | A1 | 8/2012 | Seibel et al. |
| 2014/0065034 | A1* | 3/2014 | Zheng ................ G01N 30/6095 422/502 |
| 2014/0308179 | A1* | 10/2014 | Marchiarullo .. A61L 35/150305 422/527 |
| 2015/0248109 | A1* | 9/2015 | Mathuis ................. C12M 41/36 359/370 |
| 2015/0293010 | A1* | 10/2015 | Nagrath ............ B01L 3/502753 435/34 |

OTHER PUBLICATIONS

Baker, Principles of Biologial Microtechnique, Richard Clay and Company, Ltd., Suffolk, England, 386 pages, 1958.

Baldwin, et al., "Measurements of the anisotropy of ultrasonic velocity in freshly excised and formalin-fixed myocardial tissue," Journal of the Acoustical Society of America, 118(1):505-513, 2005.

Bauer, et al., "Dynamic subnanosecond time-of-flight detection for ultra-precise diffusion monitoring and optimization of biomarker preservation," Proceedings of SPIE, Medical Imaging 2014: Ultrasonic Imaging and Tomography, vol. 9040, pp. 90400B-1-90400B-10, 2014.

Boskovic, et al., "Pneumothorax after transthoracic needle biopsy of lung lesions under CT guidance," Journal of Thoracic Disease, vol. 6, Suppl 1, pp. S99-S107, 2014.

Brentnall, "Arousal of cancer-associated stromal fibroblasts: palladin-activated fibroblasts promote tumor invasion," Cell Adhesion & Migration, vol. 6, No. 6, pp. 488-494, 2012.

Brentnall, et al., "Arousal of cancer-associated stroma: overexpression of palladin activates fibroblasts to promote tumor invasion," PLoS One, vol. 7, No. 1, e30219, 2012.

Brown, "The science and application of hematoxylin and eoisin staining," Robert H. Lurie Comprehensive Cancer Center, pp. 1-92, 2013.

Bui, et al., "Revisiting optical clearing with dimethyl sulfoxide (DMSO)," Lasers in Surgery and Medicine, vol. 41, No. 2, pp. 142-148, 2009.

Bussolati, et al.,"Formalin fixation at low temperature better preserves nucleic acid integrity," PLoS One, vol. 6, No. 6, : e21043, 2011.

Calhoun, et al., "Needle Biopsy for Breast Cancer Diagnosis: A Quality Metric for Breast Surgical Practice," Journal of Clinical Oncology, vol. 32, No. 21, pp. 2191-2192, 2014.

Cano, et al., "Pancreatic development and disease," Gastroenterology, vol. 132, No. 2, pp. 745-762, 2007.

Carson, "Fixation," in Histotechnology: A Self-Instructional Text, 2nd Ed., American Society for Clinical Pathology, pp. 1-24, 1997.

Carvalho, et al., "Predictions and measurements of laminar flow over two-dimensional obstacles," Applied Mathematical Modeling, vol. 11, No. 1, pp. 23-34, 1987.

Cavanna, et al., "Role of Guided—Fine Needle Biopsy of the Pancreatic Lesion," in Pancreatic Cancer—Clinical Management, Prof. Sanjay Srivastava (Ed.), pp. 237-254, ISBN: 978-953-51-0394-3, 2012.

Chang, et al., "A Microfluidic Device for Exposing Tumor Biopsy Tissue to Multiple Drugs," Proceedings of the 16th International Conference on Miniaturized Systems for Chemistry and Life Sciences (MICROTAS '12), pp. 815-817, 2012.

Chen, et al., "Quantifying elasticity and viscosity from measurement of shear wave speed dispersion," The Journal of the Acoustical Society of America, vol. 115, No. 6, pp. 2781-2785, 2004.

Choi, et al., "Determination of chemical agent optical clearing potential using in vitro human skin," Lasers in Surgery and Medicine, vol. 36, No. 2, pp. 72-75, 2005.

Chou, et al., "3D imaging of fine needle aspirates using optical projection tomographic microscopy," Journal of Cytology & Histology, S2:001, pp. 1-4, 2012.

Chu, et al., "Ultrasound-accelerated formalin fixation of tissue improves morphology, antigen and mRNA preservation," Modern Pathology, vol. 18, No. 6, pp. 850-863, 2005.

Coe, et al., "Isometric 3D imaging of cellular samples using optical projection tomographic microscopy," Advanced Biophotonics: Tissue Optical Sectioning, pp. 581-620, 2013.

Constantin, et al., "Percutaneous US-guided renal biopsy: a retrospective study comparing the 16-gauge end-cut and 14-gauge side-notch needles," Journal of Vascular and Interventional Radiology, vol. 21, No. 3, pp. 357-361, 2010.

Colace et al. (Jul. 2013) "Microfluidics and coagulation biology," Annual Review of Biomedical Engineering, 15:283-303.

Dan, et al., "A Novel Method for Preparation of Tissue Microarray," World Journal of Gastroenterology, vol. 10, No. 4, pp. 579-582, 2004.

Das, et al., "Beyond isolated cells: microfluidic transport of large tissue for pancreatic cancer diagnosis," Proceedings of SPIE, Microfluidics, BioMEMS, and Medical Microsystems XIII, 9320:93200N-1-93200N-15, 2015.

Das, et al., "Feasibility of a hybrid elastographic-microfluidic device to rapidly process and assess pancreatic cancer biopsies for pathologists," 2014 IEEE Health Innovations and Point-of-Care Technologies Conference (HIC), pp. 271-275, 2014.

Das, et al., "Optical clearing and registration of thick pancreas specimens: a first step to 3D imaging of tissue biopsy," Proceedings of the Biomedical Engineering Society (BMES) 2013 Annual Meeting, p. 175, 2013.

Das, et al., "Optically clearing tissue as an initial step for 3D imaging of core biopsies to diagnose pancreatic cancer," Proceedings of SPIE, Optical Interactions with Tissue and Cells XXV; and Terahertz for Biomedical Applications, vol. 3941, pp. 89410N-1-89410N-11, 2014.

Das, et al., "Pathology in a tube: Step 1. Fixing, staining and transporting pancreatic core biopsies in a microfluidic levice for 3D imaging," Proceedings of SPIE, Microfluidics, BioMEMS, and Medical Microsystems XII, 8976:89760R-1-89760R-8, doi: 10.1117/12.2041106, 2014.

Dempster, "Rates of penetration of fixing fluids," American Journal of Anatomy, vol. 107, No. 1, pp. 59-72, 1960.

Diao, et al., "A three-channel microfluidic device for generating static linear gradients and its application to the quantitative analysis of bacterial chemotaxis," Lab on a Chip, vol. 6, No. 3, pp. 381-388, 2006.

(56) References Cited

OTHER PUBLICATIONS

Diederich, et al., "Application of a single needle type for all image-guided biopsies: results of 100 consecutive core biopsies in various organs using a novel tri-axial, end-cut needle," Cancer Imaging, vol. 6, No. 1, pp. 43-50, 2006.
Dogan, et al., "Can we obtain better specimens with an end-cutting prostatic biopsy device?" European Urology, vol. 17, No. 3, pp. 297-301, 2005.
Durst, et al., "Investigations of laminar flow in a pipe with sudden contraction of cross sectional area," Computers and Fluids, vol. 13, No. 1, pp. 15-36, 1985.
Ellenrieder et al. (2004; retrieved May 2017) "Fibrogenesis in the pancreas," Roczniki Akademii Medycznej w Bialymstoku, 49:40-46.
Fajardo, et al., "Fragmentation of prostatic needle biopsy cores containing adenocarcinoma: the role of specimen submission," BJU International, vol. 105, No. 2, pp. 172-75, 2010.
Finn, "Diagnostic pathology and laboratory medicine in the age of "omits": a paper from the 2006 William Beaumont Hospital Symposium on Molecular Pathology," The Journal of Molecular Diagnostics, vol. 9, No. 4, pp. 431-436, 2007.
Fox, et al., "Formaldehyde fixation," Journal of Histochemistry and Cytochemistry, vol. 33, No. 8, pp. 845-853, 1985.
Frulio, et al., "Ultrasound elastography in liver," Diagnostic and Interventional Imaging, vol. 94, No. 5, pp. 515-534, 2013.
Fu, et al., "Three-dimensional optical method for integrated visualization of mouse islet microstructure and vascular network with subcellular-level resolution," Journal of Biomedical Optics, vol. 15, No. 4, pp. 046018-1-046018-9, 2010.
Gann, et al., "Risk factors for prostate cancer detection after a negative biopsy: a novel multivariable longitudinal approach," Journal of Clinical Oncology, vol. 28, No. 10, pp. 1714-1720, 2010.
Genina et al., "Tissue optical immersion clearing," Expert Review of Medical Devices, vol. 7, No. 6, pp. 825-842, 2010.
Gharib, et al., "Chapter 6d. Fine-Needle Aspiration Biopsy of the Thyroid Gland," Thyroid Disease Manager, pp. 1-24, available online at: http://www.thyroidmanager.orgichapter/fine-needle-aspiration-biopsy-of-the-thyroid-gland/, 2012.
Gutwein, et al., "Utilization of minimally invasive breast biopsy for the evaluation of suspicious breast lesions," The American Journal of Surgery, vol. 202, No. 2, pp. 127-132, 2011.
Haggarth, et al., "A new core-biopsy instrument with an end-cut technique provides prostate biopsies with increased issue yield," BJU International, vol. 90, No. 1, pp. 51-55, 2002.
Hariri, et al., "In vivo optical coherence tomography: the role of the pathologist," Archives of Pathology and Laboratory Medicine, vol. 136, No. 12, pp. 1492-1501, 2012.
Hattori, et al., "Pressure-driven microfluidic perfusion culture device for integrated dose-response assays," Journal of Laboratory Automation, vol. 18, No. 6, pp. 437-445, 2013.
Hirshburg, et al., "Molecular basis for optical clearing of collagenous tissues," Journal of Biomedical Optics, vol. 15, No. 5, pp. 055002-1-055002-8, 2010.
Hopper, et al., "CT percutaneous biopsy guns: comparison of end-cut and side-notch devices in cadaveric specimens," American Journal of Roentgenology, vol. 164, No. 1, pp. 195-199, 1995.
Hsieh, et al., "Liquid flow in a micro-channel," Journal of Micromechanics and Microengineering, vol. 14, No. 4, pp. 136-445, 2004.
Hwang, et al., "Optical coherence tomography imaging of the pancreas: a needle-based approach," Clinical Gastroenterology and Hepatology, vol. 3, No. 7 Suppl 1, pp. S49-S52, 2005.
Iglesia-Garcia, et al., "Feasibility and yield of a new EUS histology needle: results from a multicenter, pooled, cohort study," Gastrointestinal Endoscopy, vol. 73, No. 6, pp. 1189-1196, 2011.
Inamdar, "Laminar and turbulent flows," University of Delaware, EGTE215/BREG15: Applied Fluid Mechanics Lecture, available online at: http://udel.edu/~inamdar/EGTE215/Laminar_turbulent. pdf, 2012.
Kawada, et al., "Potential use of point shear wave elastography for the pancreas: a single center prospective study," European Journal of Radiology, vol. 83, No. 4, pp. 620-624, 2014.
Kim, et al., "US-guided Fine-Needle Aspiration of Thyroid Nodules: Indications, Techniques, Results 1," Radiographics, vol. 28, No. 7, pp. 1869-1886, 2008.
Koch, et al., "Ultrasound velocity and attenuation of porcine soft tissues with respect to structure and composition: I. Muscle," Meat Science, vol. 88, No. 1, pp. 51-58. doi: 10.1016/j.meatsci.2010.12. 002, 2011.
Kruss, et al., "Circular, nanostructured and biofunctionalized hydrogel microchannels for dynamic cell adhesion studies," Lab on a Chip, vol. 12, No. 18, pp. 3285-3289, 2012.
Kumar, et al., "Mechanics, malignancy, and metastasis: the force journey of a tumor cell," Cancer and Metastasis Reviews, vol. 28, No. 1-2, pp. 113-127, 2009.
Kwon, "High Throughput 3-D Tissue Cytometry," Massachusetts Institute of Technology, PhD Dissertation, 102 pages, 2007.
Kwon, et al., "Quantitative morphometric measurements using site selective image cytometry of intact tissue," Journal of the Royal Society Interface, vol. 6, No. 1, pp. S45-S57, 2009.
Lee, et al., "Microfluidic devices with permeable polymer barriers for capture and transport of biomolecules and cells," Lab on a Chip, vol. 13, No. 17, pp. 3389-3397, 2013.
Li, et al., "Classification of colorectal polyp regions in optical projection tomography," 2013 IEEE 10th International Symposium on Biomedical Imaging, pp. 736-739, 2013.
Liang, et al., "Modeling and measurement of tissue elastic moduli using optical coherence elastography," Proceedings of SPIE, Optics in Tissue Engineering and Regenerative Medicine II, vol. 6858, pp. 685803-1-685803-8, 2008.
Loeb, et al., "Complications after prostate biopsy: data from Seer-Medicare," The Journal of Urology, vol. 186, No. 5, pp. 1830-1834, 2011.
Login, "Microwave fixation provides excellent preservation of tissue, cells and antigens for light and electron microscopy," Histochemical Journal, vol. 20, No. 6-7, pp. 373-387, 1988.
Ma, "Credit card-sized device could analyze biopsy, help diagnose pancreatic cancer in minutes," UW Today, available online at: http://www.washington.edu/news/2014/02/06/credit-card-sized-device-could-analyze-biopsy-help-diagnose-pancreatic-cancer-in-minutes/, 2014.
McCormack, et al. "Effect of needle size on cancer detection, pain, bleeding and infection in TRUS-guided prostate biopsies: a prospective trial," Canadian Urological Association Journal, vol. 6, No. 2, pp. 97-101., 2012.
McGhee, et al., "Formaldehyde as a probe of DNA structure. 3. Equilibrium denaturation of DNA and synthetic polynucleotides," Biochemistry, vol. 16, No. 15, pp. 3267-3276, 1977.
Medawar, "III.—The Rate of Penetration of Fixatives," Journal of the Royal Microscopical Society / Journal of Microscopy, vol. 61, No. 1-2, pp. 46-57, 1941.
Miao, et al., "Dual-modal optical projection tomography microscopy for cancer diagnosis," Proceedings of SPIE, Three-Dimensional and Multidimensional Microscopy: Image Acquisition and Processing XVII, vol. 7570, pp. 75700H-1-15700H-7, 2010.
Miao, et al., "Dual-modal optical projection tomography microscopy for cancer diagnosis," Proceedings of SPIE, Three-Dimensional and Multidimensional Microscopy: Image Acquisition and Processing, vol. XVII, pp. 7570:75700H-1-15700H-7, 2010.
Miao, et al., "Dual-modal three-dimensional imaging of single cells with isometric high resolution using an optical Drojection tomography microscope," Journal of Biomedical Optics, vol. 14, No. 6, pp. 064035-1-064035-6, 2009.
Miao, et al., "Dual-mode optical projection tomography microscope using gold nanorods and hematoxylin-stained cancer cells," Optics Letters, 35(7):1037-1039, 2010.
Miao, et al., "High resolution optical projection tomographic microscopy for 3D tissue imaging," Proceedings of SPIE, Three-Dimensional and Multidimensional Microscopy: Image Acquisition and Processing XVIII, vol. 7904, pp. 74040L-1-74040L-5, 2011.
Miao, et al., "High resolution optical projection tomographic microscopy for 3D tissue imaging," Proceedings of SPIE, Three-

(56) References Cited

OTHER PUBLICATIONS

Dimensional and Multidimensional Microscopy: Image Acquisition and Processing, vol. XVIII, No. 7904, pp. 79040L-1-79040L-5, 2011.
Miao, et al., "Multimodal 3D imaging of cells and tissue, bridging the gap between clinical and research microscopy," Annals of Biomedical Engineering, 40(2):263-276, 2012.
Miller, et al., "Confocal imaging of the embryonic heart: how deep?" Microscopy and Microanalysis, vol. 11, No. 3, pp. 216-223, 2005.
Monici, "Cell and tissue autofluorescence research and diagnostic applications," Biotechnology Annual Review, 11:227-256, 2005.
Moore, "Tissue cutting in needle biopsy," University of Michigan, PhD Dissertation, 103 pages, 2011.
Moy, et al., "Optical Histology: a method to visualize microvasculature in thick tissue sections of mouse brain," PLoS One, vol. 8, No. 1, e53753, 2013.
Mushate, "Study of 2-D laminar flow in a pipe with a sudden contraction of cross sectional area," Engineering & Technology, vol. 25, No. 1, pp. 1-8, 2007.
Nassar, "Core needle biopsy versus fine needle aspiration biopsy in breast—a historical perspective and opportunities in the modern era," Diagnostic Cytopathology, vol. 39, No. 5, pp. 380-388, 2011.
Nguyen, et al., "Shear wave pulse compression for dynamic elastography using phase-sensitive optical coherence tomography," Journal of Biomedical Optics, vol. 19, No. 1, pp. 016013-1-016013-6, 2014.
Nicolle, et al., "Shear mechanical properties of the porcine pancreas: experiment and analytical modelling," Journal of the Mechanical Behavior of Biomedical Materials, vol. 26, pp. 90-97, 2013.
Norton, et al., "3D architecture of ductal carcinoma in situ from image reconstructions," IEEE EMBS Conference on Biomedical Engineering and Sciences (IECBES), pp. 631-635, 2012.
Oldham, et al., "Optical clearing of unsectioned specimens for three-dimensional imaging via optical transmission and emission tomography," Journal of Biomedical Optics, vol. 13, No. 2, pp. 021113-1-021113-8, 2008.
Olson, et al., "Cancer. Breaching the cancer fortress," Science, vol. 324, No. 5933, pp. 1400-1401, 2009.
Ophir, et al., "Elastography: a quantitative method for imaging the elasticity of biological tissues," Ultrasonic Imaging, vol. 13, No. 2, pp. 111-134, 1991.
Ozden, et al., "The long core needle with an end-cut technique for prostate biopsy: does it really have advantages when compared with standard needles?" European Urology, vol. 45, No. 3, pp. 287-291, 2004.
Park, et al., "A dual-modality optical coherence tomography and fluorescence lifetime imaging microscopy system for simultaneous morphological and biochemical tissue characterization," Biomedical Optics Express, vol. 1, No. 1, pp. 186-200, 2010.
Parra, et al., "Multiphoton microscopy of cleared mouse brain expressing YFP," Journal of Visualized Experiments, vol. 67, :e384, 2012.
Parra, et al., "Multiphoton microscopy of cleared mouse organs," Journal of Biomedical Optics, vol. 15, No. 3, pp. 336017-1-036017-5, 2010.
Paszek and VM Weaver (Oct. 2004) "The tension mounts: mechanics meets morphogenesis and malignancy," Journal of Mammary Gland Biology and Neoplasia, 9(4):325-342, 2004.
Paul, et al., "Mo1489 EUS Guided Fine Needle Aspiration (EUS-FNA) Versus Fine Needle Biopsy (EUS FNB): a Comparison of Technical Success, Efficacy and Cost Analysis for Pancreas Masses," Gastrointestinal Endoscopy, 2013.
Pienaar, "Viscous flow through sudden contractions," Cape Peninsula University of Technology, PhD Dissertation, 263 pages, 2004.
Poepping, et al., "A thin-walled carotid vessel phantom for Doppler ultrasound flow studies," Ultrasound in Medicine & Biology, vol. 30, No. 8, pp. 1067-1078, 2004.
Ragan, et al., "High-resolution whole organ imaging using two-photon tissue cytometry," Journal of Biomedical Optics, vol. 12, No. 1, pp. 014015-1-014015-9, 2007.

Randolph-Habecker, "Tips about fixation and formalin," available online at: https://sharedresources.fredhutch.org/training/tips-about-fixation-and-formalin, 2013.
Reis, et al., "The impact of core biopsy fragmentation in prostate cancer," International Urology and Nephrology, vol. 12, No. 4, pp. 965-969, 2010.
Rolls, "Fixation and fixatives (1)—the process of fixation and the nature of fixatives," Leica Biosystems, available online at: http://www.leicabiosystems.com/pathologyleaders/fixation-and-fixatives-1-the-process-of-fixation-and-the-nature-of-fixatives/, 2012.
Rolls, "Fixation and fixatives (2)—factors influencing chemical fixation, formaldehyde and glutaraldehyde," Leica Biosystems, available online at: http://www.leicabiosystems.com/pathologyleaders/fixation-and-fixatives-2-factors-influencing-chemical-fixation-formaldehyde-and-glutaraldehyde/, 2012.
Rolls, "Fixation and fixatives (5)—practical procedures to optimise quality, the effects of heat and microwaves," Leica Biosystems, available online at: http://www.leicabiosystems.com/pathologyleaders/fixation-and-fixatives-5-practical-procedures-to-optimise-quality-the-effects-of-heat-and-microwaves/, 2012.
Safneck, et al., "Fixation Techniques for Fine Needle Aspiration Biopsy Smears Prepared Off Site," Acta Cytologica, vol. 45, No. 3, pp. 365-371, 2001.
Saisho, et al., "Pancreas volumes in humans from birth to age one hundred taking into account sex, obesity and presence of type-2 diabetes," Clinical Anatomy, vol. 20, No. 8, pp. 933-942, 2007.
Samani, et al., "Elastic moduli of normal and pathological human breast tissues: an inversion-technique-based investigation of 169 samples," Physics in Medicine and Biology, vol. 52, No. 6, pp. 1565-1576, 2007.
Schaefer, "The normal weight of the pancreas in the adult human being: A biometric study," The Anatomical Record, vol. 32, No. 2, pp. 119-132, 1926.
Schiffhauer, et al., "Confocal microscopy of unfixed breast needle core biopsies: a comparison to fixed and stained sections," BMC Cancer, vol. 9, No. 265, pp. 1-10, 2009.
Sen, "Diffusion and tissue microstructure," Journal of Physics: Condensed Matter, vol. 16, No. 44, pp. S5213-S5220, 2004.
Sharpe, et al., "Optical projection tomography as a tool for 3D microscopy and gene expression studies," Science, vol. 296, No. 5567, pp. 541-545, 2002.
Shidham, et al., "Tissue Harvester with Functional Valve (THFV): Shidham's Device for Reproducibly Higher Specimen Yield by Fine Needle Aspiration Biopsy with Easy to Perform Steps," BMC Clinical Pathology, vol. 7, No. 2, 2007.
Shidham, et al., 2004) "Optimization of an Immunostaining Protocol for the Rapid Intraoperative Evaluation of Melanoma Sentinel Lymph Node Imprint Smears with the 'MCW Melanoma Cocktail'," CytoJoumal, vol. 1, No. 1, pp. 2, 2004.
Shung, et al., "Ultrasonic scattering from tissues," Proceedings of the 1977 IEEE Ultrasonics Symposium, Paper No. 77CH1264-1SU: pp. 230-233, 1977.
Shung, et al., "Ultrasound velocity in major bovine blood vessel walls." Journal of the Acoustical Society of America, vol. 64, No. 2, pp. 692-694, 1978.
Siegel, et al., "Cancer statistics, 2012," CA: A Cancer Journal for Clinicians, 62(1):10-29, 2012.
Silverstein, "Where's the outrage?" Journal of the American College of Surgeons, vol. 208, No. 1, pp. 78-79, 2009.
Song, et al., "Shear modulus imaging by direct visualization of propagating shear waves with phase-sensitive optical coherence tomography," Journal of Biomedical Optics, vol. 18, No. 12, pp. 121509-1-121509-7, 2013.
Start, et al., "Reassessment of the rate of fixative diffusion," Journal of Clinical Pathology, vol. 45, No. 12, pp. 1120-1121, 1992.
Sun, et al., "Comparison of fine-needle aspiration cytology and core biopsy for diagnosis of breast cancer," Diagnostic Cytopathology, vol. 24, No. 6, pp. 421-425, 2001.
Suresh, "Biomechanics and biophysics of cancer cells," Acta Biomaterialia, vol. 3, No. 4, pp. 413-438, 2007.

(56) References Cited

OTHER PUBLICATIONS

Tanter, et al., "Quantitative assessment of breast lesion viscoelasticity: initial clinical results using supersonic shear imaging," Ultrasound in Medicine and Biology, vol. 34, No. 9, pp. 1373-1386, 2008.
Testoni, et al., "Optical coherence tomography for bile and pancreatic duct imaging," Gastrointestinal Endoscopy Clinics of North America, 19(4):637-653, 2009.
Thavarajah, et al., "Chemical and physical basics of routine formaldehyde fixation." Journal of Oral and Maxillofacial Pathology, vol. 16, No. 3, pp. 400-405, 2012.
Tilli, et al.(Sep.-Oct. 2007) "Realtime imaging and characterization of human breast tissue by reflectance confocal microscopy," Journal of Biomedical Optics, vol. 12, No. 5, pp. 051901-1-051901-10, 2007.
Tuchin, Optical Clearing of Tissues and Blood, SPIE Press, PM154:ix-12, 2005.
Ubhayakar, et al., "Improving glandular covering during prostate biopsy using a long-core needle: technical performance of an end-cutting needle," BJU International, vol. 89, No. 1, pp. 40-43, 2002.
Underhill, "V.—The Rate of Penetration of Fixatives," Journal of the Royal Microscopical Society / Journal of Microscopy, vol. 52, No. 2, pp. 113-120, 1932.
Voung, et al., "3D optical coherence tomography and digital pathology," 2011 International Quantum Electronics Conference & Lasers and Electro-Optics (CLEO/IQEC/PACIFIC RIM), pp. 685-687, 2011.
Wang, et al., "Concurrent enhancement of imaging depth and contrast for optical coherence tomography by hyperosmotic agents," Journal of the Optical Society of America B, vol. 18, No. 7, pp. 948-953, 2001.
Wang, et al., "Photoacoustic tomography: in vivo imaging from organelles to organs," Science, vol. 335, No. 6075, pp. 1458-1462, 2012.
Webster, et al., "A Microfluidic Device for Tissue Biopsy Culture and Interrogation," Analytical Methods, vol. 2, No. 8, pp. 1005-1007, 2010.
Wehking, "Pressure losses experienced by liquid flow through PDMS microchannels with abrupt area changes," University of Central Florida, Master's Thesis, 145 pages, 2008.
Werner, et al., "Effect of formalin tissue fixation and processing on immunohistochemistry." The American Journal of Surgical Pathology, vol. 24, No. 7, pp. 1016-1019, 2000.
Wolf, "Chapter 94: Evaluation of the Size, Shape, and Consistency of the Liver," Clinical Methods: The History, Physical, and Laboratory Examinations, pp. 478-481, 1990.
Yang, et al., "Traffic of leukocytes in microfluidic channels with rectangular and rounded cross-sections," Lab on a Chip, vol. 11, No. 19, pp. 3231-3240, 2011.
Yao, et al., "In vivo label-free photoacoustic microscopy of cell nuclei by excitation of DNA and RNA," Optics Letters, vol. 35, No. 24, pp. 4139-4141, 2010.
Young, et al., "Fundamentals of microfluidic cell culture in controlled microenvironments," Chemical Society Reviews, vol. 39, No. 3, pp. 1036-1048, 2010.
Zacharakis, et al., "Characterization of biopsy samples with optical computed tomography," 2011 International Workshop on BioPhotonics, pp. 1-3, 2011.
Zhou, et al.: "PMN-PT single crystal, high-frequency ultrasonic needle transducers for pulsed-wave Doppler application," IEEE Transactions on Ultrasonics, Ferroelectrics, and Frequency Control, vol. 54, No. 3, pp. 668-675, 2007.
Apesteguia and LJ Pina (Aug. 2011) "Ultrasound-guided core-needle biopsy of breast lesions," Insights Into Imaging, 2 (4):493-500.
Burfeind et al. (2013; retrieved May 2017) "Microfluidic device development and analysis to prepare bulk pancreas tissue for 3D imaging," Proceedings of the Biomedical Engineering Society (BMES) 2013 Annual Meeting, p. 175.
Chalfi (Jul. 2007) "Pressure loss associated with flow area change in micro-channels," Georgia Institute of Technology, Master's Thesis, 93 pages.
Chen et al. (Aug. 2012) "Stromal galectin-1 expression is associated with long-term survival in resectable pancreatic ductal adenocarcinoma," Cancer Biology & Therapy, 13(10):899-907.
Chesnick et al. (Oct. 2010) "Elevated pressure improves the rate of formalin penetration while preserving tissue morphology," Journal of Cancer, 1:178-183.
Hovhannisyan et al. (Apr. 2013) "Elucidation of the mechanisms of optical clearing in collagen tissue with multiphoton imaging," Journal of Biomedical Optics, 18(4):046004.
Neumann et al. (Aug. 2008) "Simultaneous 3D imaging of morphology and nanoparticle distribution in single cells with the Cell-CT technology," Proceedings of the 30th Annual International Conference of the IEEE Engineering in Medicine and Biology Society (IEEE EMBS), pp. 379-381.

\* cited by examiner

FLUIDIC DEVICE AND METHODS OF USE FOR PROCESSING TISSUE FOR PATHOLOGY

CROSS-REFERENCE TO RELATED APPLICATIONS

This application claims priority to (i) U.S. Provisional Patent Application No. 62/111,236, filed Feb. 3, 2015, and (ii) U.S. Provisional Patent Application No. 62/239,619, filed on Oct. 9, 2015, both of which are hereby incorporated by reference in their entirety.

GOVERNMENT RIGHTS

This invention was made with government support under grant number CBET-1212540 awarded by the National Science Foundation and grant number R21 CA186791-01 awarded by the National Institutes of Health. The government has certain rights in the invention.

BACKGROUND

Unless otherwise indicated herein, the materials described in this section are not prior art to the claims in this application and are not admitted to be prior art by inclusion in this section.

To determine a diagnosis for various diseases, pathologists typically obtain biopsies from patients, which are first processed in large-scale pathology laboratories and then assessed after specimens are observed in two-dimensions (2D) through a microscope using white light. Thinly sectioned 2D core biopsies, which are chunks of biological tissue, contain the most information that best represents the in vivo condition of a disease state. However, 2D slides are inherently distorted and disorienting when observed by pathologists, hence significant tissue architectural information is lost.

Three-dimensional (3D) imaging aids pathologists by providing an even more complete picture of the disease state, which promotes rapid on site evaluation and enhances diagnostic accuracy. However, manual handling of bulk biological tissue samples required for 3D imaging is difficult due to tissue viscoelasticity. Consequently, fixing, staining, and optical clearing of such biological tissue samples is inherently time intensive. These factors have been raised by clinicians as major limitations for the rapid processing and throughput of intact, 3D biological tissue samples to be used for diagnosis and study. Therefore, a fluidic device and methods of use for processing such 3D biological tissue samples for pathology may be desirable.

SUMMARY

Example devices and methods described herein describe various fluidic devices. In one aspect, a fluidic device is provided including (a) a plurality of channels including one or more curved channels having a channel input and a channel output, wherein the one or more curved channels have a substantially circular cross-section, (b) an input interface between the channel input of the one or more curved channels and an exterior of the fluidic device, wherein the input interface is configured to receive a biological tissue sample, and (c) an output interface between the channel output of the one or more curved channels and the exterior of the fluidic device.

In a second aspect, a method is provided. The method may include providing an aqueous liquid to one or more curved channels of a fluidic device to contact a biological tissue sample, wherein a flow rate of the aqueous liquid through the one or more curved channels is greater than a threshold flow rate, and wherein the biological tissue sample passes through the one or more curved channels to the output interface of the fluidic device when the flow rate is greater than the threshold flow rate.

In a third aspect, a fluidic device is provided including (a) a channel configured to receive a biological tissue sample, wherein the channel includes a transparent window, (b) an actuator configured to provide shear waves to the biological tissue sample positioned in the channel, and (c) an optical coherence tomography device positioned adjacent to the transparent window, wherein the optical coherence tomography device is configured to measure a shear wave speed within the biological tissue sample.

In a fourth aspect, a method is provided. The method may include (a) providing shear waves to a biological tissue sample positioned within a channel, (b) determining a shear wave speed within the biological tissue sample, (c) based on the determined shear wave speed, determining a shear modulus of the biological tissue sample, and (d) in response to the determined shear modulus of the biological tissue sample exceeding a threshold shear modulus value, determining fixation of the biological tissue sample is complete.

These as well as other aspects, advantages, and alternatives, will become apparent to those of ordinary skill in the art by reading the following detailed description, with reference where appropriate to the accompanying drawings.

DETAILED DESCRIPTION

Example methods and systems are described herein. It should be understood that the words "example," "exemplary," and "illustrative" are used herein to mean "serving as an example, instance, or illustration." Any embodiment or feature described herein as being an "example," being "exemplary," or being "illustrative" is not necessarily to be construed as preferred or advantageous over other embodiments or features. The example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the Figures should not be viewed as limiting. It should be understood that other embodiments may include more or less of each element shown in a given Figure. Further, some of the illustrated elements may be combined or omitted. Yet further, an example embodiment may include elements that are not illustrated in the Figures.

As used herein, "curved channel" means a channel having at least one segment that is not straight.

As used herein, "substantially stationary" means movement less than about ±1 mm/min.

As used herein, "liquid fixative" means any fixative known in the art, including, but not limited to, formaldehyde, glutaraldehyde, formalin, alcohol, acetic acid, and mixtures thereof.

As used herein, "liquid dye" means any known histological dyes known in the art, including, but not limited to, methylene blue, hematoxylin, eosin, Congo red, and Janis green.

As used herein, "liquid optical clearing agent" means any optical clearing agent known in the art, including, but not limited to, solutions which contain alcohols such as glycerol and/or various dilutions of glyercol in phosphate-buffered saline, solutions which contain sugars, such as sucrose, solutions which contain solvents, such as xylene, dimethyl sulfoxide liquid (DMSO), and other liquids of high refractive index that reduce optical scattering is tissues, such as benzyl alcohol and benzyl benzoate (BABB), methyl salicylate, cedar wood oil, wood oil, or various mixtures thereof.

As used herein, with respect to measurements, "about" means+/−5%.

Figure 1A:
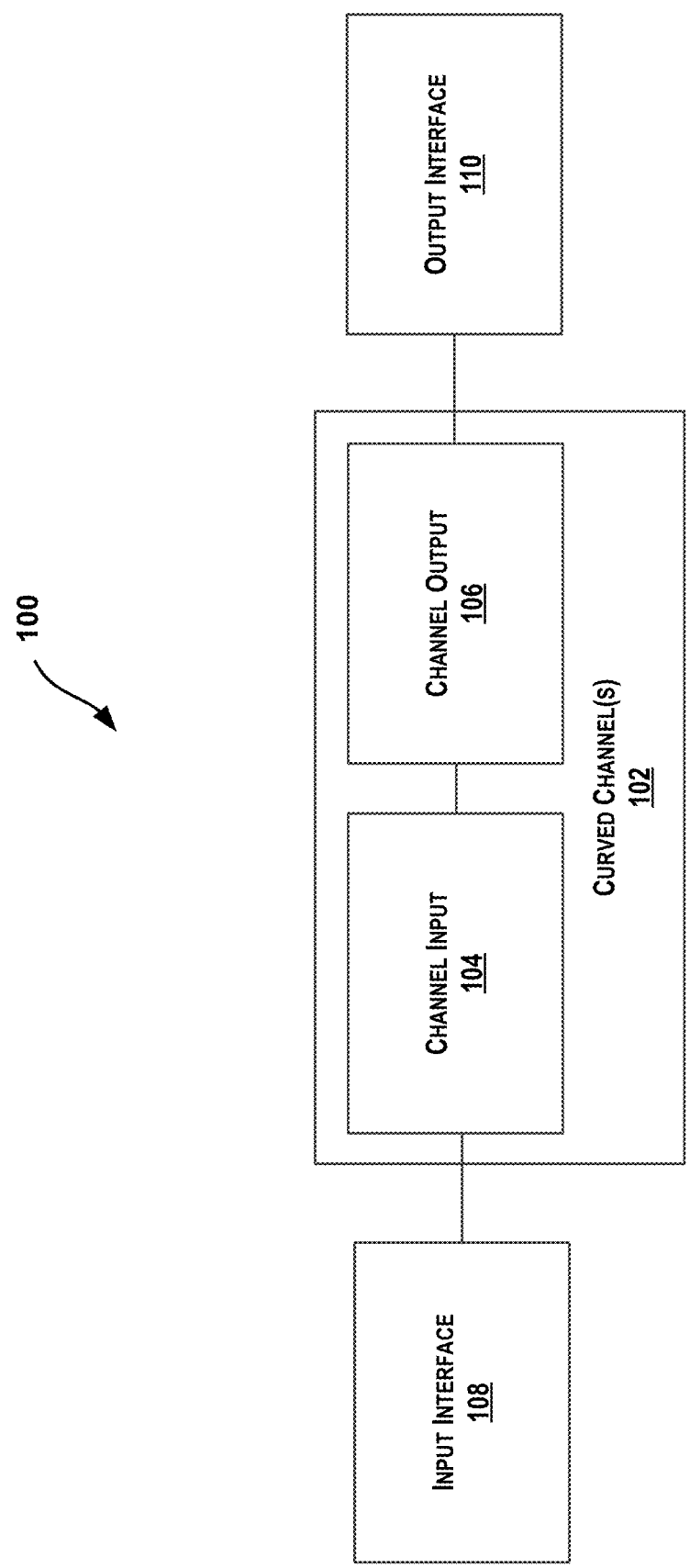
FIG. 1A illustrates a simplified block diagram of a fluidic device, according to an example embodiment.

With reference to the Figures, FIG. 1A illustrates an example fluidic device 100. The fluidic device 100 may include a plurality of channels including one or more curved channels 102. Each of such curved channels 102 may include a channel input 104 and a channel output 106. In addition, each of such curved channels 102 may have a substantially circular cross-section. The fluidic device 100 may also include an input interface 108 between the channel input 104 of the curved channel(s) 102 and an exterior of the fluidic device 100. The fluidic device 100 may also include an output interface 110 between the channel output 106 of the curved channel(s) 102 and the exterior of the fluidic device 100.

Figure 1B:
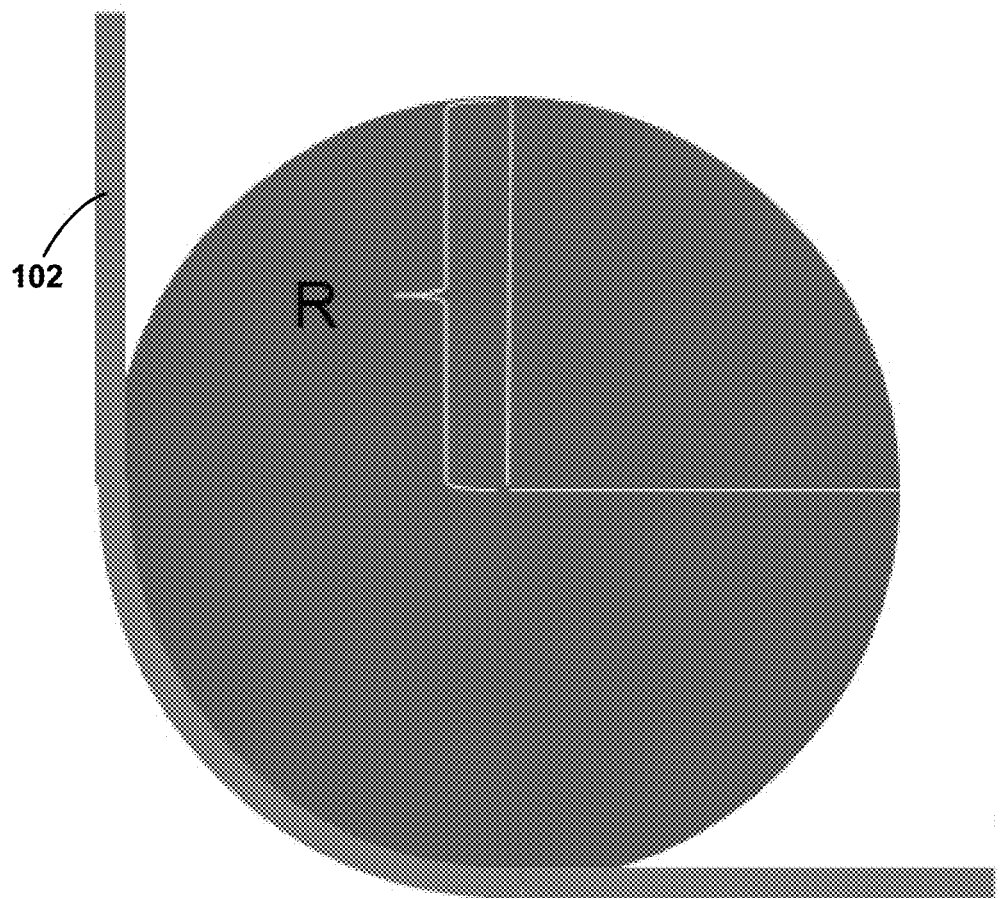
FIG. 1B illustrates a radius of curvature of a curved channel of the fluidic device, according to an example embodiment.

The curved channel(s) 102 may have a radius of curvature between about 0.5 cm and about 10 cm, as examples. As shown in FIG. 1B, the radius of curvature R of a given curved channel 102 is a measure of the radius of the circular arc which best approximates the curved segment of the curved channel 102. As such, the curved channel 102 is bound by the arc of the circle. Thus, a curved channel 102 having a radius of curvature of 0.5 cm would have a tighter curve while a curved channel 102 having a radius of curvature of 10 cm would have a more gradual curve. In addition, the curved channel(s) 102 may have a length between about 1 cm and about 10 cm. Further, the curved channel(s) 102 may have a diameter between about 0.2 mm and about 5 mm.

The input interface 108 and the output interface 110 may provide a fluid-tight connection mechanism to couple the fluidic device 100 to other components. For example, the input interface 108 may be configured to couple the curved channel 102 of the fluidic device 100 to a coring needle such that the fluidic device can received a biological tissue sample from the coring needle. The output interface may be configured to couple the curved channel 102 to an imaging system for further evaluation of the biological tissue sample.

In operation, the input interface 108 may be configured to receive a biological tissue sample as discussed above. In one example, the input interface 108 may include a one-way septum to provide a sealed interface between the channel input 104 and the exterior of the fluidic device 100. In such an example, a pathologist can pass the biological tissue sample from a coring needle, through the input interface 108, and into the curved channel 102. In such an example, the coring needle may be attached to a formalin-filled syringe prior to the deposition of the biological tissue sample into the fluidic device 100. In this fashion, fixative may be continuously diffusing into the biological tissue sample while the coring needle's contents are gently positioned into the channel input 104 using formalin fluid flow from the syringe. The biological tissue sample may be substantially cylindrical, and the diameter of the curved channel 102 may be 10% to 20% greater than the diameter of the biological tissue sample.

Once the biological tissue sample is positioned within the curved channel 102, the fluidic device may be configured to provide an aqueous liquid to the curved channel 102 to contact the biological tissue sample. A flow rate of the aqueous liquid through the curved channel may be greater than a threshold flow rate, such that the biological tissue sample passes through the channel 102 to the output interface 106 of the fluidic device 100. In one example, the threshold flow rate is about 5 mL/min. In such an example, the fluidic device 100 may further include a first reservoir including the aqueous solution in fluid communication with the curved channel 102. In yet another embodiment, the fluidic device 100 may further include a second reservoir including a liquid fixative in fluid communication with the curved channel 102, a third reservoir including a liquid dye in fluid communication with the curved channel 102, and a fourth reservoir including a liquid optical clearing agent in fluid communication with the curved channel, as discussed in greater detail below. Further, the fluidic device 100 may include one or more pumps in fluid communication with the first reservoir, the second reservoir, the third reservoir, and the fourth reservoir to provide a corresponding liquid to the curved channel 102 at a desired flow rate.

Figure 2A:
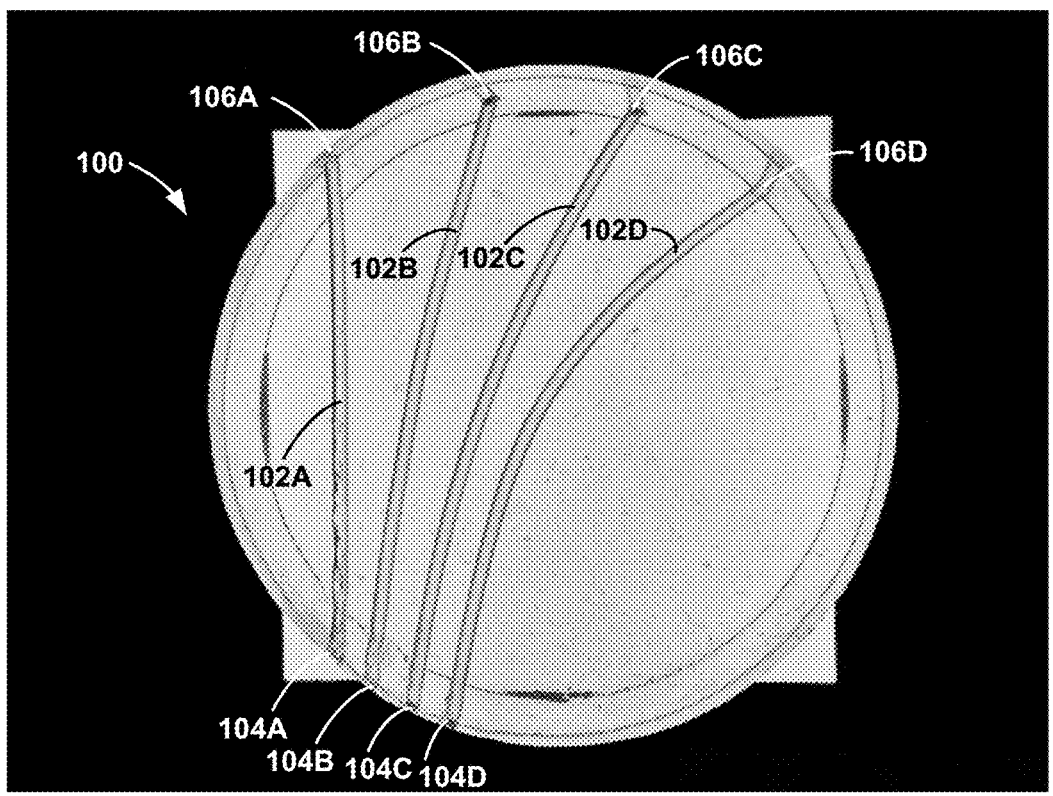
FIG. 2A illustrates a top view of a fluidic device, according to an example embodiment.
Figure 2B:
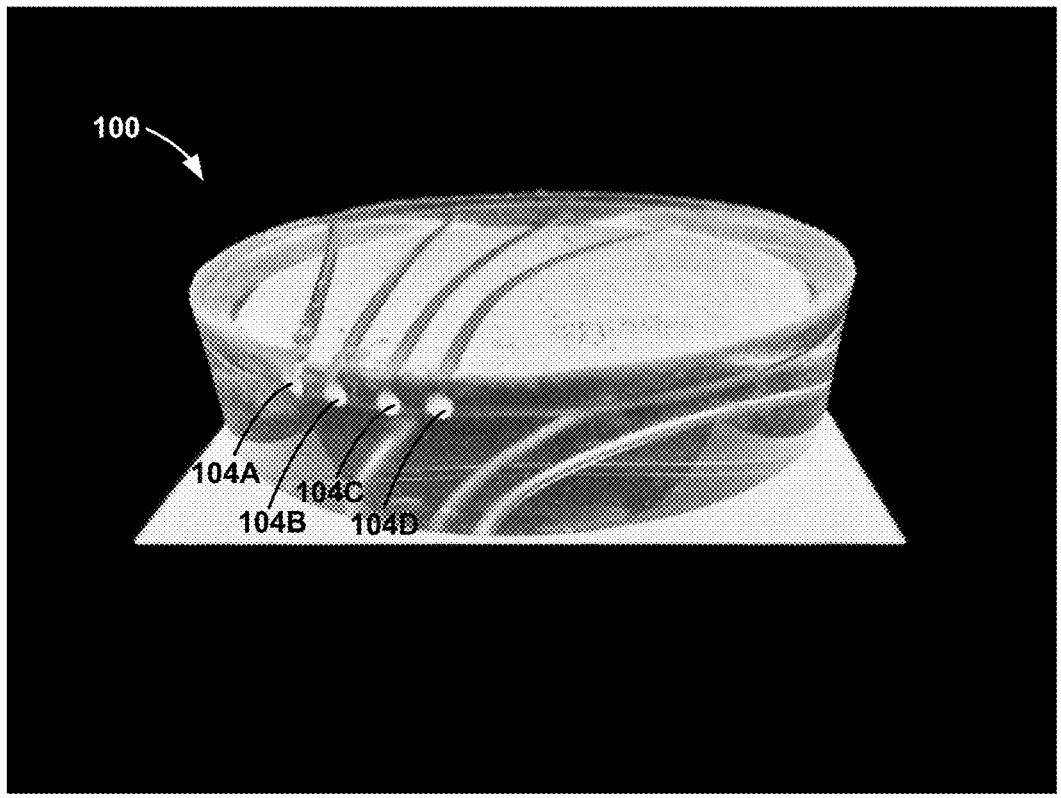
FIG. 2B illustrates a side view of the fluidic device of FIG. 2A, according to an example embodiment.
Figure 2C:
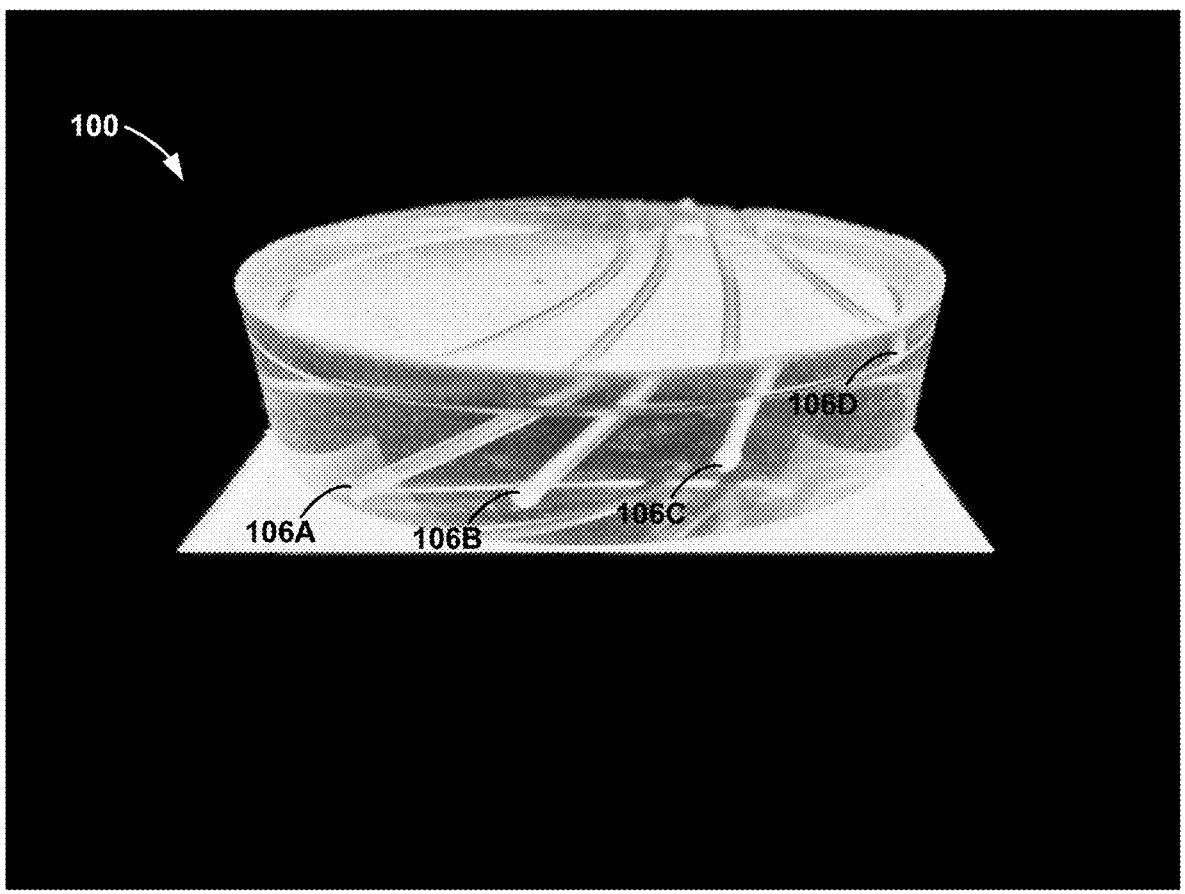
FIG. 2C illustrates a side view of the fluidic device of FIG. 2A, according to an example embodiment.

FIGS. 2A-2H illustrate example fluidic devices, according to example embodiments. In particular, FIGS. 2A-2C illustrates a top view of an example fluidic device 100. As shown in FIG. 2A, the fluidic device 100 may include four curved channels 102A-102D. Each of the four curved channels 102A-102D may be used to pass biological tissue samples from the channel inputs 104A-104D to the channel outputs 106A-106D. Further, the channel inputs 104A-104D and corresponding input interfaces may be positioned at a first height (as shown in FIG. 2B), and the channel outputs 106A-106D and corresponding output interfaces may be positioned at a second height (as shown in FIG. 2C). As shown in FIGS. 2B and 2C, the first height may be different than the second height such that the curved channels 102A-102D extend from one plane to another. Such an embodiment enables the fluidic device to include a plurality of curved channels in a compact space, thereby reducing the size of the fluidic device.

Figure 2D:
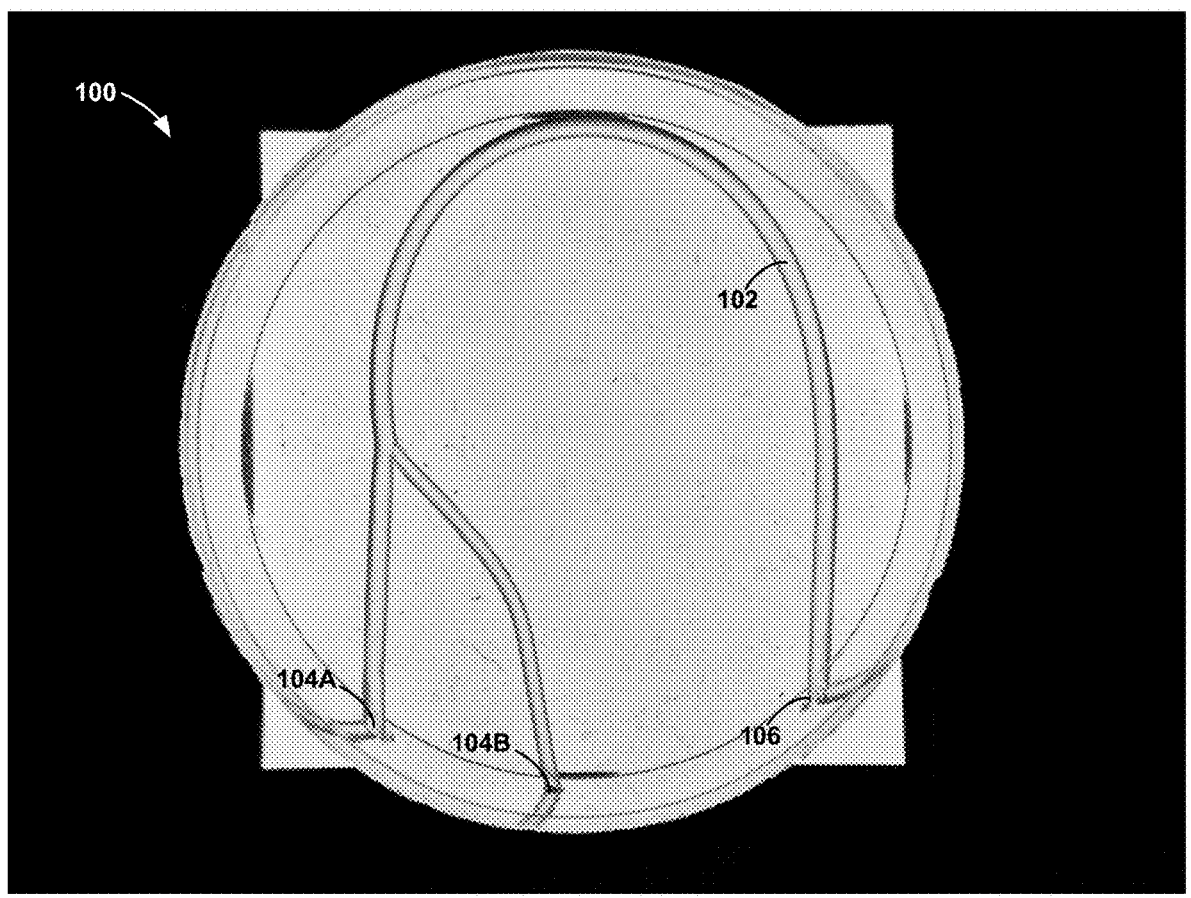
FIG. 2D illustrates a top view of another fluidic device, according to an example embodiment.

FIG. 2D illustrates another example fluidic device 100. In particular, the fluidic device 100 shown in FIG. 2D illustrates a curved channel 102 including two channel inputs 104A, 104B which converge such that there is a single channel output 106. In such an embodiment, the biological tissue sample may be passed through the first channel input 104A, while liquid fixative, liquid dye, and/or liquid optical clearing agent may be passed through the second channel input 104B. After such processing, the biological tissue sample may be passed through the curved channel 102 to the channel output 106 for further processing.

Figure 2E:
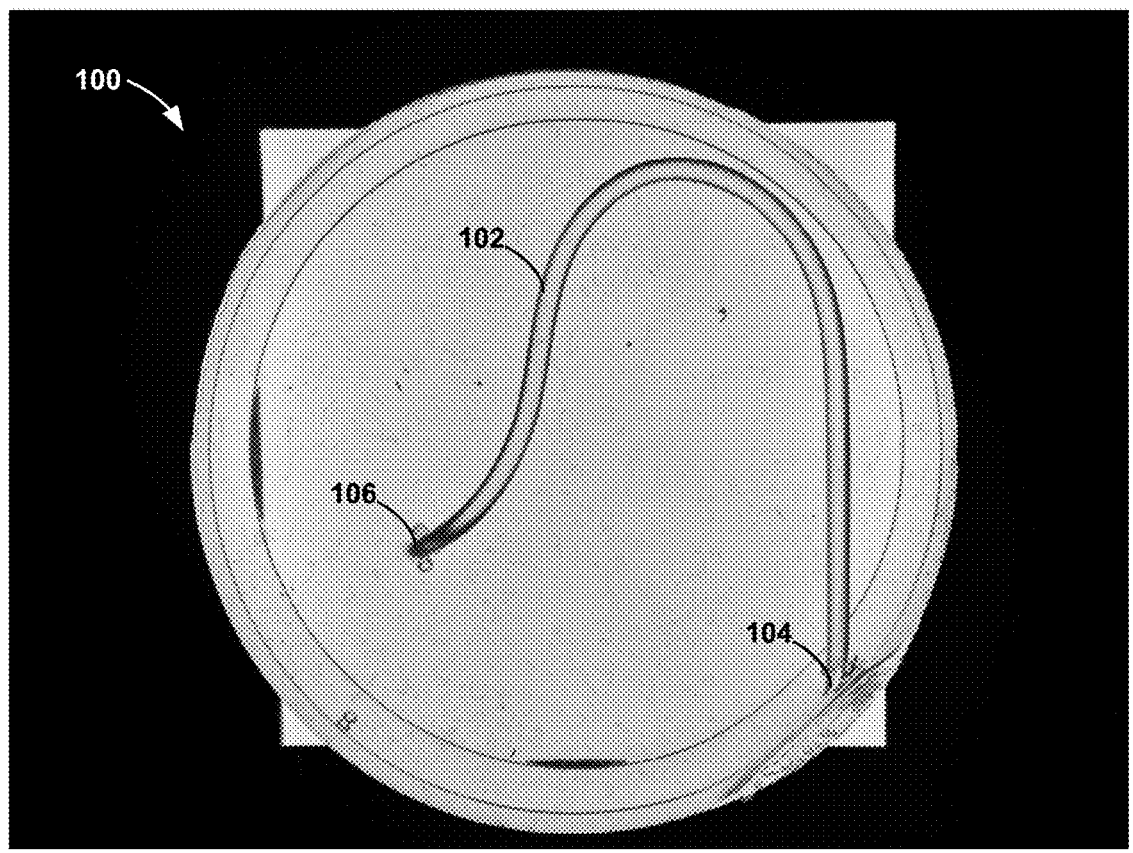
FIG. 2E illustrates a top view of another fluidic device, according to an example embodiment.
Figure 2F:
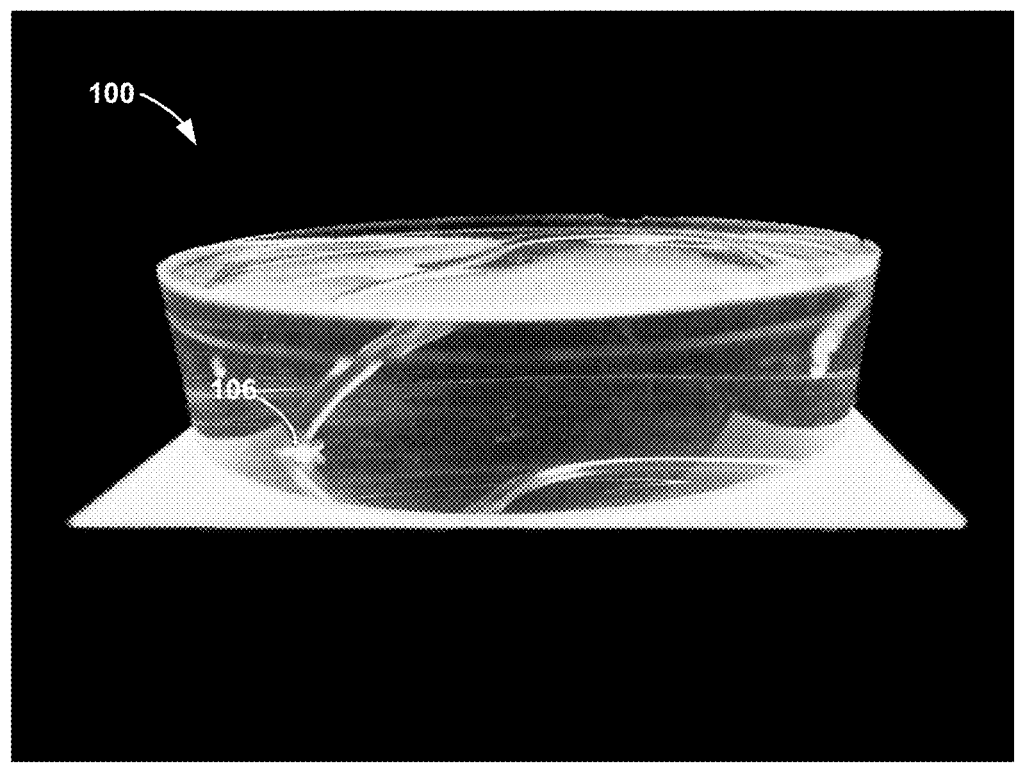
FIG. 2F illustrates a side view of the fluidic device of FIG. 2E, according to an example embodiment.
Figure 2G:
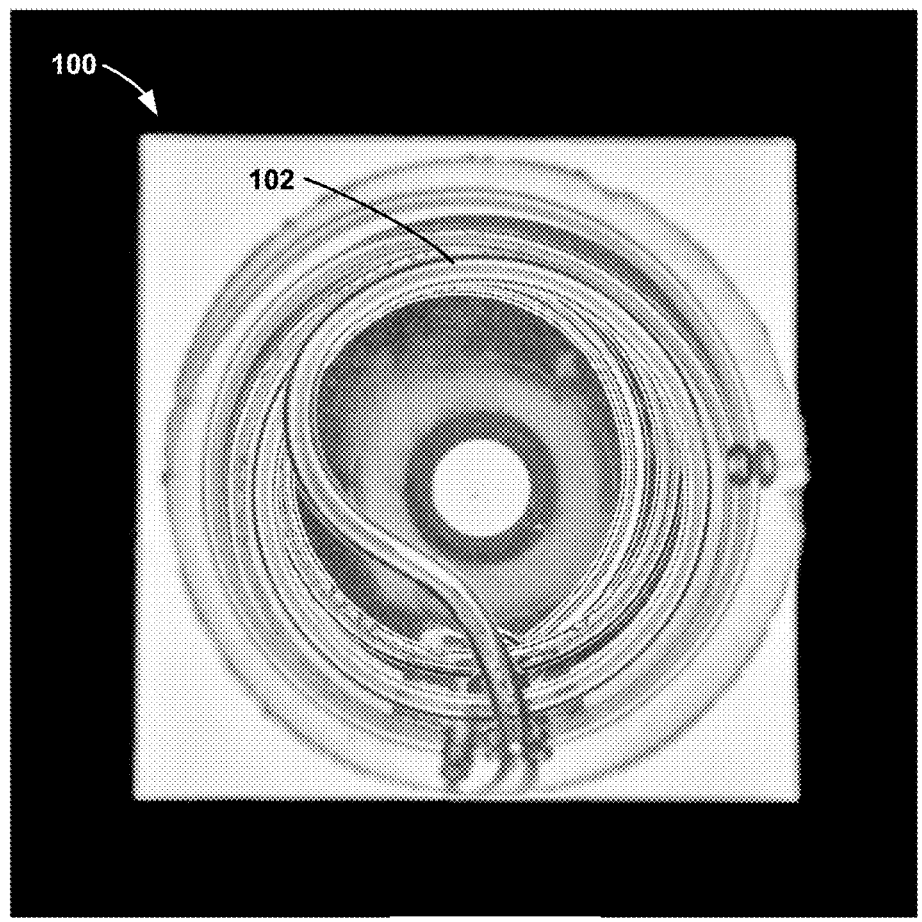
FIG. 2G illustrates a top view of another fluidic device, according to an example embodiment.
Figure 2H:
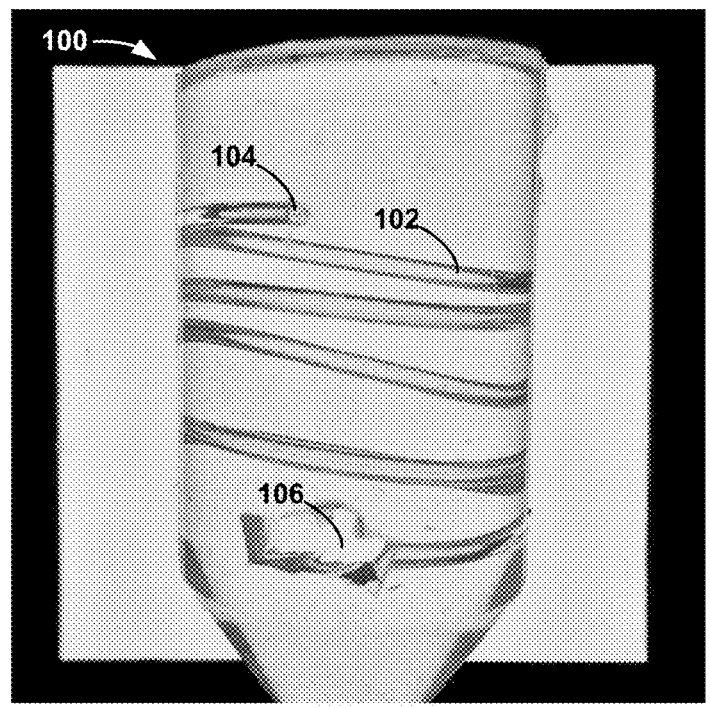
FIG. 2H illustrates a side view of the fluidic device of FIG. 2E, according to an example embodiment.

FIGS. 2E-2F illustrate another example fluidic device 100. In particular, the fluidic device 100 shown in FIGS. 2E-2F illustrate a curved channel 102 including a channel input 104 at a first height in the side of the fluidic device 100, and a channel output 106 at a second height in the bottom of the fluidic device. FIGS. 2G-2H illustrate yet another example fluidic device 100. In particular, the fluidic device 100 shown in FIGS. 2G-2H illustrate a curved channel 102 having a spiral helical shape. As such, the curved channel 102 has a channel input 104 at a first height, and a channel output 106 at a second height, where the first height is greater than the second height. The examples shown in FIGS. 2A-2H are merely examples; other fluidic channel arrangements are possible as well.

The ability to fabricate curved, circular cross-sectioned channels such as those in FIGS. 2A-2H, provide an opportunity for biological tissue samples to be transported with changes in direction and thus provides design flexibility of the fluidic device channels to better interface with external systems (e.g., imaging systems). As such, fluidic processing and 3D imaging to enhance diagnosis is no longer to limited to transporting biological tissue samples solely in a straight direction. The smooth direction changes allows for the biological tissue ample to gradually bend with the curvature of the curved channel(s) 102 to successfully transport the tissue through the curved channel(s) 102. Without the smooth curve, biological tissue samples tend to stall at direction changes. Transportation of such biological tissue samples can now be achieved in multiple directions and dimensions, thus allowing for reduction in fluidic device footprint. As such, fluidic devices incorporating such curved channels can be fit onto smaller platforms. Further, the curved channels described above in relation to FIGS. 2A-2H provide flexibility in channel path designs to incorporate necessary stages in preparation of the biological tissue sample and required instrumentation access, as discussed in more detail below. For example, the insertion of the biological tissue sample may be accomplished in the center of the fluidic device to maintain mechanical stability during needle insertion, while the diagnostic imaging of the biological tissue sample may occur near a surface of the fluidic device to provide effective access for an optical microscope.

Figure 3:
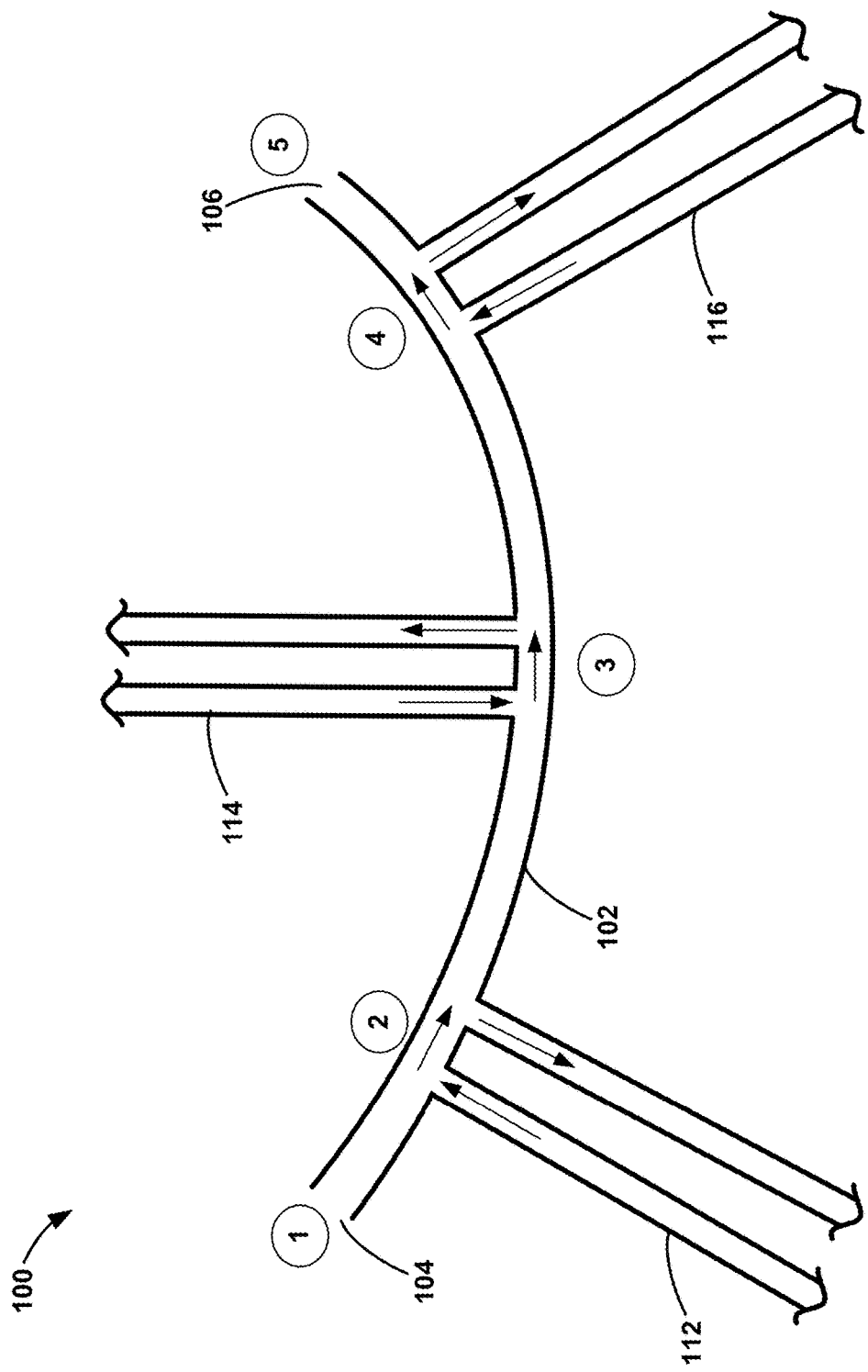
FIG. 3 illustrates an example fluidic device, according to an example embodiment.

FIG. 3 illustrates another example fluidic device 100, according to an example embodiment. As shown in FIG. 3, the fluidic device 100 includes a curved channel 102 having a channel input 104 and a channel output 106. The curved channel 102 may be in fluid communication with a first reservoir including an aqueous liquid. Further, the fluidic device includes a first U-channel 112, a second U-channel 114, and a third U-channel 116, each in fluid communication with the curved channel 102. The first U-channel 112 may be in fluid communication with a second reservoir including a liquid fixative, the second U-channel 114 may be in fluid communication with a third reservoir including a liquid dye, and the third U-channel 116 may be in fluid communication with a fourth reservoir including a liquid optical clearing agent. The fluidic device 100 may further include one or more pumps in fluid communication with one or more of the first reservoir, the second reservoir, the third reservoir, and the fourth reservoir.

In operation, a biological tissue sample may be positioned in the curved channel 112 near the channel input at position 1. The one or more pumps may cause the aqueous fluid to flow from the first reservoir to thereby pass the biological tissue sample from position 1 to position 2, at which point the aqueous fluid from the first reservoir is reduced so the biological tissue sample remains at position 2. Once at position 2, the one or more pumps may cause the liquid fixative to flow from the second reservoir to the first U-channel 112. As shown by the arrows in FIG. 3, the liquid fixative may pass from a first branch of the first U-channel 112, through the curved channel 102, and to a second branch of the first U-channel 112. The flow rate of the liquid fixative through the curved channel 102 may be below a threshold flow rate such that the biological tissue sample remains in position 2 while the liquid fixative contacts the biological tissue sample.

Next, the one or more pumps may cause the aqueous fluid to flow from the first reservoir to thereby pass the biological tissue sample from position 2 to position 3, at which point the aqueous fluid from the first reservoir is reduced so the biological tissue sample remains at position 3. Once at position 3, the one or more pumps may cause the liquid dye to flow from the third reservoir to the second U-channel 114. As shown by the arrows in FIG. 3, the liquid dye may pass from a first branch of the second U-channel 114, through the curved channel 102, and to a second branch of the second U-channel 114. The flow rate of the liquid dye through the curved channel 102 may be below the threshold flow rate such that the biological tissue sample remains in position 3 while the liquid fixative contacts the biological tissue sample.

Next, the one or more pumps may cause the aqueous fluid to flow from the first reservoir to thereby pass the biological tissue sample from position 3 to position 4, at which point the aqueous fluid from the first reservoir is reduced so the biological tissue sample remains at position 4. Once at position 4, the one or more pumps may cause the liquid optical clearing agent to flow from the fourth reservoir to the third U-channel 116. As shown by the arrows in FIG. 3, the liquid optical clearing agent may pass from a first branch of the third U-channel 116, through the curved channel 102, and to a second branch of the third U-channel 116. The flow rate of the liquid optical clearing agent through the curved channel 102 may be below the threshold flow rate such that the biological tissue sample remains in position 4 while the liquid fixative contacts the biological tissue sample.

Finally, the one or more pumps may cause the aqueous fluid to flow from the first reservoir to thereby pass the biological tissue sample from position 4 to position 5 out of the channel outlet 106.

Figure 4:
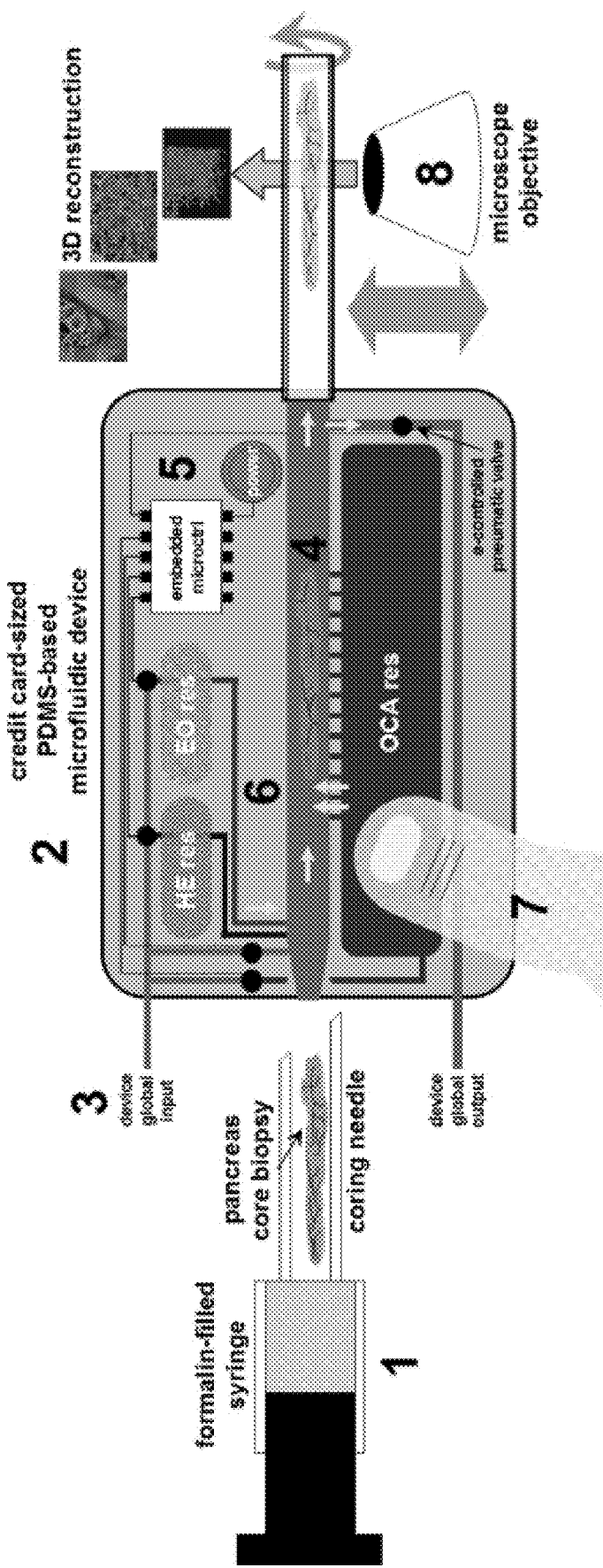
FIG. 4 illustrates yet another example fluidic device, according to an example embodiment.

FIG. 4 illustrates yet another example fluidic device 2, according to an example embodiment. As shown in FIG. 4, the fluidic device 2 is a poly(dimethylsiloxane) (PDMS)-based fluidic device including a channel input to streamline geometry and reduce device footprint. A formalin-filled syringe 1 may be coupled to a coring needle, which includes the biological tissue sample. The coring needle may be press fit into a puckered septum, and the biological tissue sample can then be deposited into the main channel of the fluidic device. Initially, fixative, stain, and OCA may flow through dedicated channels with color camera monitoring. After flow characteristics are optimized, channels may be regulated by valves 5 controlled by a microcontroller. In another embodiment, on-board stain and OCA reservoirs may be driven by pressing on compliant regions, thus making the fluidic device mobile and low-cost as there are no moving parts. Finally, the biological tissue sample will be transported via fluid flow to a microscopic objective 8 for further imaging and 3D reconstruction.

In another embodiment, the fluidic devices described in FIGS. 1-4 may further include variations in cross-section. In such examples, the one or more curved channels may include at least a first segment and a second segment, where the first segment has a diameter that is different than that of the second segment. The first segment can be of any suitable length, variability, etc. Further, each of the curved channels may include more than two segments, such as three, four, or five segments with multiple regions of variability. Such cross-sectional area constrictions promote the ability to measure mechanical properties of the specimen and evaluation of tissue health, i.e. viscoelasticity, stiffness, connectivity, elasticity and evaluation of the structural architecture of the extracellular matrix (and integrity) of the biological tissue sample. Such variable diameters may function as valves with no significant moving parts that aid fluid flow with respect to tissue processing, staining and transport. Variable diameters may also function as regions of direct physical interrogation, such as manual manipulation for transport, manual staining, or tissue separation (in cases where samples were improperly procured by the clinical coring needle).

In another embodiment, the fluidic devices described in FIGS. 1-4 may further include a flexible window. In one example, the flexible window comprises PDMS having a thickness between about 0.1 mm and about 1 mm. Such a flexible window is pliable and retains known radiative transport properties. In such an example, the fluidic device may further include an imaging device positioned adjacent to the flexible window. Such an imaging device may take many forms, including but not limited to, a smartphone camera, an all-purpose digital camera, a machine vision camera (e.g., a CCD, or CMOS sensor with an attached fixed focus lens), or a standalone optoelectric component, such as an LED transmitter and a photodiode, a phototransistor, or a photoresistor detector (e.g., transmitter-detector couples).

Such an imaging device may be configured to measure transparency of the biological tissue sample. Further, the flexible window may enable measurements of, mechanical force, stiffness and elastic properties to further assess opto-mechanical integrity while the biological tissue sample remains sealed within the fluidic chamber. Radiative properties of such flexible windows will permit direct, quantitative measurement of local forces, stiffnesses, densities and elastic properties of the biological tissue sample.

In yet another example, the fluidic devices described in FIGS. 1-4 may further include an actuator configured to provide shear waves to the biological tissue sample. Such an actuator may be a piezoelectric actuator that contacts the biological tissue sample. In such an example, the fluidic device further includes an optical coherence tomography device configured to measure shear wave speed within the biological tissue.

Figure 5:
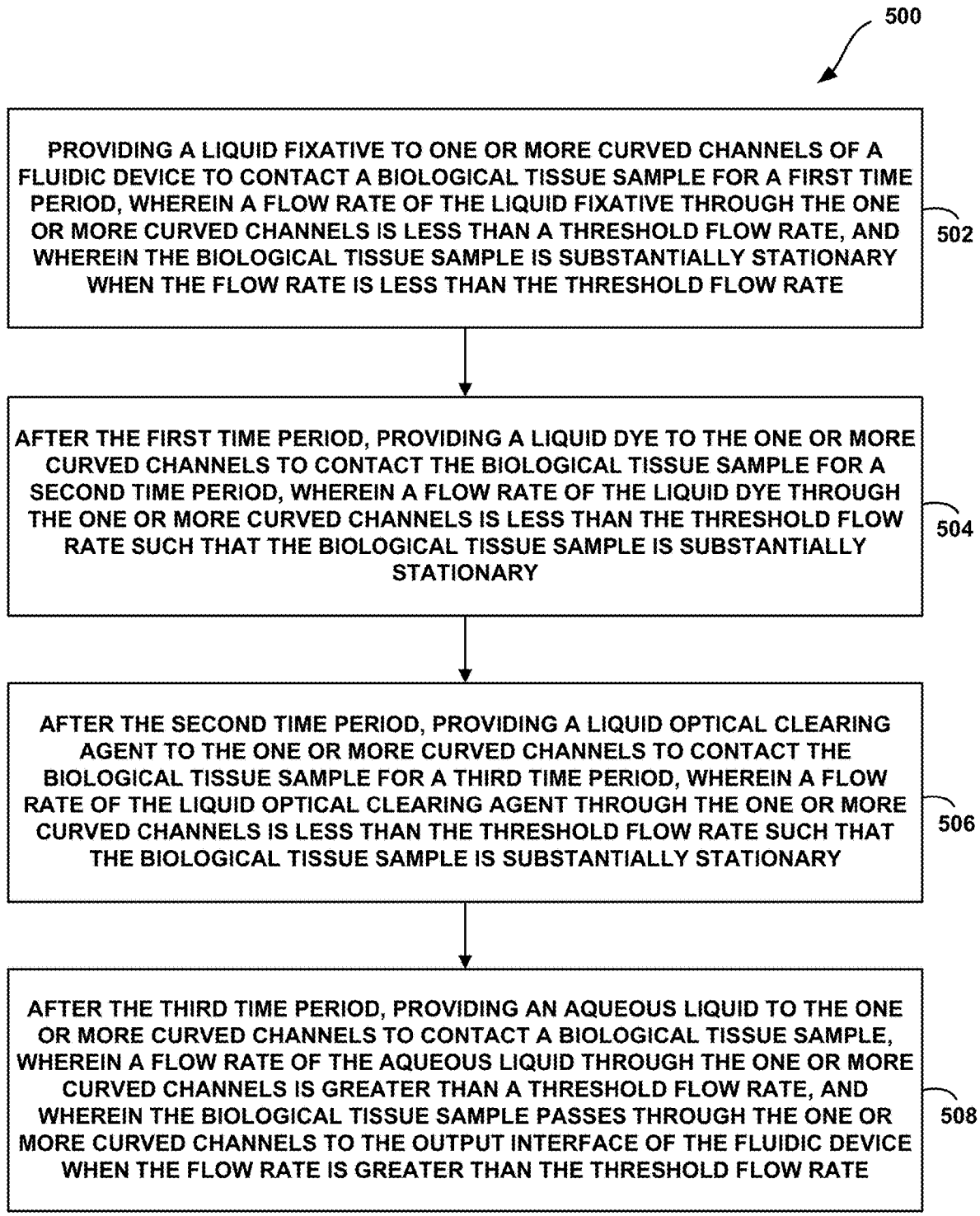
FIG. 5 is a flowchart illustrating an example method according to an example embodiment.

FIG. 5 is a block diagram of an example method for preparing and transporting a biological tissue sample for pathology. Method 500 shown in FIG. 5 presents an embodiment of a method that could be used by the fluidic devices described in FIGS. 1-4, as examples. Method 500 may include one or more operations, functions, or actions as illustrated by one or more of blocks 502-508. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

In addition, for the method 500 and other processes and methods disclosed herein, the block diagram shows functionality and operation of one possible implementation of present embodiments. In this regard, each block may represent a module, a segment, or a portion of program code, which includes one or more instructions executable by a processor or computing device for implementing specific logical functions or steps in the process. The program code may be stored on any type of computer readable medium, for example, such as a storage device including a disk or hard drive. The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device.

Initially, at block 502, the method 500 includes providing a liquid fixative to one or more curved channels of a fluidic device to contact a biological tissue sample for a first time period, wherein a flow rate of the liquid fixative through the one or more curved channels is less than a threshold flow rate, and wherein the biological tissue sample is substantially stationary when the flow rate is less than the threshold flow rate. The liquid fixative may be any fixative known in the art, including, but not limited to, formaldehyde, glutaraldehyde, formalin, alcohol, acetic acid, and mixtures thereof.

As described above in relation to FIG. 1B, the curved channel(s) may have a radius of curvature between about 0.5 cm and about 10 cm. In addition, the curved channel(s) may have a length between about 1 cm and about 10 cm, and a diameter between about 0.2 mm and about 5 mm. The biological tissue sample may be substantially cylindrical, and the diameter of the curved channel(s) may be about 10% to about 20% greater than the diameter of the biological tissue sample. The threshold flow rate may be about 5 mL/min, such that the biological tissue sample is substantially stationary if the flow rate in the curved channel is less than about 5 mL/min. In one example, the first time period is between about 1 minute and about 120 minutes.

Laminar fluid fixative flow continuously infuses the fluid volume adjacent to the biological tissue sample with fresh liquid fixative and therefore maintains the local environment at a constant fixative concentration. The liquid fixative may be presented to the biological tissue sample in various ways. In one example, the liquid fixative flows through the main curved channel where tissue transport occurs. In another example, as shown in FIG. 3, the liquid fixative is delivered through a U-channel along the length of the curved channel. Other examples are possible as well.

In one embodiment, the method further includes heating the one or more curved channels during the first time period such that the liquid fixative is at a temperature between about 21° C. and 50° C., and preferably between about 40° C. and 50° C. The curved channel may be heated through resistive wiring surrounding the curved channel, for example. Heating the curved channel may reduce the chemical fixation or optical clearing times for the biological tissue sample. In another embodiment, the method further includes providing microwaves to the one or more curved channels during the first time period. In such an example, a specialty, or general purpose microwave may be employed during fixation. The entire fluidic device after being placed in the microwave oven and may be exposed to microwave radiation between tens of milliseconds to several minutes as desired by the pathologist. Exposing the biological tissue sample to microwaves during fixation may reduce the fixation time for the biological tissue sample.

In yet another embodiment, the method further includes providing ultrasonic waves to the one or more curved channels during the first time period. In such an example, a metal probe may be inserted into the microfluidic channel. The metal probe may be a piezoelectric actuator, as an example. The metal probe makes direct physical contact with the biological tissue sample in the curved channel. Ultrasonic waves may be applied to the biological tissue sample prior to and during fixation. In another example, the entire fluidic device may also be placed into the container of an ultrasonicator, which provides uniform, unilateral application of ultrasound throughout the entire device during fixation or optical clearing. Exposing the biological tissue sample to ultrasonic waves during fixation or optical clearing may reduce the time required for the biological tissue sample to be fixed or cleared.

At block 504, the method 500 includes, after the first time period, providing a liquid dye to the one or more curved channels to contact the biological tissue sample for a second time period, wherein a flow rate of the liquid dye through the one or more curved channels is less than the threshold flow rate such that the biological tissue sample is substantially stationary. The liquid dye may include any known histological dyes known in the art, including, but not limited to, methylene blue, hematoxylin, eosin, Texas red, standard DAPI dyes, Congo red, and Janis green. In one example, the second time period is between about 1 minute and about 120 minutes.

Laminar fluid dye flow continuously infuses the fluid volume adjacent to the biological tissue sample with fresh liquid dye and therefore maintains the local environment at a constant dye concentration. The liquid dye may be presented to the biological tissue sample in various ways. In one example, the liquid dye flows through the main curved channel where tissue transport occurs. In another example, as shown in FIG. 3, the liquid dye is delivered through a U-channel along the length of the curved channel. Other examples are possible as well.

To increase contrast of salient tissue features, stains may be applied to biopsies stationed within the microfluidics device for brightfield and fluorescence microscopy. The goal is to develop automated color labeling of tissue features using one or more stains while biological tissue sample is within the fluidic device. By applying flow within the curved channel of the fluidic device, dye diffusion may be enhancing by controlling the residence time of dye molecules at the lateral surface of the biological tissue sample. In this fashion, liquid dyes will flow alongside specimens with camera monitoring. To provide homogeneous staining, a short burst of weak acid may be added to ensure peripheral tissue layers are stained similarly to the innermost layers of the biopsy. For fluorescence observations, collagen autofluorescence may be employed in addition to Texas red and standard DAPI dyes, which may be used to label stromal and nuclear targets, respectively. These liquid dyes define tissue microarchitecture and specifically identify targets, which are both critical for diagnosis and also essential for prognosis and personalized treatment planning.

Next, at block 506, the method 500 includes, after the second time period, providing a liquid optical clearing agent to the one or more curved channels to contact the biological tissue sample for a third time period, wherein a flow rate of the liquid optical clearing agent through the one or more curved channels is less than the threshold flow rate such that the biological tissue sample is substantially stationary. The liquid optical clearing agent may include any optical clearing agent known in the art, including, but not limited to, solutions which contain alcohols such as glycerol and/or various dilutions of glyercol in phosphate-buffered saline, solutions which contain sugars, such as sucrose, solutions which contain solvents, such as xylene, dimethyl sulfoxide liquid (DMSO), and other liquids of high refractive index that reduce optical scattering is tissues, such as benzyl alcohol and benzyl benzoate (BABB), methyl salicylate, cedar wood oil, wood oil, or various mixtures thereof. In one example, the first time period is between about 1 minute and about 60 minutes.

Laminar optical clearing agent flow continuously infuses the fluid volume adjacent to the biological tissue sample with fresh optical clearing agent and therefore maintains the local environment at a constant optical clearing agent concentration. The liquid optical clearing agent may be presented to the biological tissue sample in various ways. In one example, the liquid optical clearing agent flows through the main curved channel where tissue transport occurs. In another example, as shown in FIG. 3, the liquid optical clearing agent is delivered through a U-channel along the length of the curved channel. Other examples are possible as well. Optical clearing dramatically reduces light scattering thereby increasing light transmission and the ability to observe deeper into thick tissues. Clearing efficacy and staining within the microfluidics device may be monitored optically by white light under the microscope using an imaging device, such as a CCD color camera. The time required for sufficient optical clearing can be enhanced by applying chemicals such as thiazone, penetrating heat such as optical radiation, and mechanical agitation such as sonic and ultrasonic energy.

Finally, at block 508, the method 500 includes, after the third time period, providing an aqueous liquid to the one or more curved channels to contact a biological tissue sample, wherein a flow rate of the aqueous liquid through the one or more curved channels is greater than a threshold flow rate, and wherein the biological tissue sample passes through the one or more curved channels to the output interface of the fluidic device when the flow rate is greater than the threshold flow rate. In one example, the flow rate of the aqueous liquid may be between about 5 mL/min and about 15 mL/min. By abruptly increasing the flow rate (5-15 mL/min), convective acceleration will dominate and generate a pressure gradient across the biological tissue sample. If the abrupt increase is short in time and the flow rate is high, the developed gradient will accelerate the core into motion. A stop in flow of the aqueous solution will result in an immediate arrest of the motion due to the dominance of viscous forces.

In one embodiment, the method may further include (i) measuring, via an imaging device, a first transparency of the biological tissue sample at the beginning of the third time period, (ii) measuring, via the imaging device, a second transparency of the biological tissue sample at the end of the third time period, and (iii) in response to the second transparency exceeding the first transparency by at least five times, providing the aqueous liquid to the one or more curved channels to contact the biological tissue sample. As described above, the imaging device may take various forms, including but not limited to, a smartphone camera, an all-purpose digital camera, a machine vision camera (e.g., a CCD, or CMOS sensor with an attached fixed focus lens), or a standalone optoelectric component, such as an LED transmitter and a photodiode, a phototransistor, or a photoresistor detector (e.g., transmitter-detector couples).

In another embodiment, the method may further include (i) measuring, via an imaging device, an intensity profile of the biological tissue sample at the end of the third time period, (ii) if the intensity profile exceeds a threshold intensity profile value, then passing the biological tissue sample through the one or more curved channels via the aqueous liquid to a three-dimensional imaging device, and (iii) if the intensity profile does not exceed the threshold intensity profile value, then passing the biological tissue sample through the one or more curved channels via the aqueous liquid to a two-dimensional imaging device. The imaging device may be any of the imaging devices described above, for example. Such a method may help determine if the biological tissue sample is sufficiently intact for 3D imaging. To make such a determination, the imaging device may determine if the biological tissue sample is one continuous piece, and if such areas are also optically intact.

To combine mechanical integrity and optical continuity (intactness quotient) into a single measurement, an intensity profile may be determined by the imaging device at the centerline of biological tissue sample illuminated with bright white light. Normalizing to background lighting, intact biological tissue samples may have similar intensities across centerlines since commercial needles will ensure constant tissue thickness. Subsequently, holes, breaks, or discontinuities within the biological tissue sample may be visible as large deviations in value that approach background intensity. A threshold may be defined by taking a profile's average intensity (Iavg) and adding two times the standard deviation (2Iσ). Thus, centerline deviations greater than Iavg+2Iσ may constitute a hole in the biological tissue sample and/or an optical/mechanical weak point that will reduce 3D imaging quality, and subsequent image stitching and registration. If centerline profiles are less than Iavg+2Iσ, core biopsies will be considered optomechanically intact and imaged in 3D via OPTM and z-stack imaging. Biopsies failing this criterion will not be discarded, but additionally processed for conventional pathology and 2D imaging/observations, thereby maximizing biospecimen utility and incorporating our process within the established workflow of pathology labs.

In yet another embodiment, the method may further include, (i) after the first time period, providing shear waves to the biological tissue sample, (ii) determining a shear wave speed within the biological tissue sample, (iii) based on the determined shear wave speed, determining a shear modulus of the biological tissue sample, and (iv) in response to the determined shear modulus of the biological tissue sample exceeding a threshold shear modulus value, providing the liquid dye to the one or more curved channels to contact the biological tissue sample. In such an example, the fluidic device may include a piezoelectric actuator that contacts the biological tissue sample to provide the shear waves to the biological tissue sample. The piezoelectric actuator may be placed preferentially in a more vertical position to produce transverse oscillations.

Further, in such an example, the fluidic device further includes an optical coherence tomography (OCT) device configured to measure shear wave speed within the biological tissue. The top surface of the curved channel may include a flexible window comprising a thin (<0.2 mm), flexible PDMS membrane in order to ascertain if OCT imaging, or propagating shear wave was significantly impacted by the substrate. In one particular example, the shear wave propagation may be tracked at a frame rate of 44.8 kHz using a phase-sensitive optical coherence tomography device. The local propagation speed of the shear wave may be calculated at each pixel of the imaging plane. The shear wave speed (v) is known to be related to soft tissue stiffness (i.e., $E \sim 3\mu = 3\rho v^2$, where E=Young's modulus, $\mu$=shear modulus and $\rho$=density). Then, shear modulus ($\mu$) may be calculated based on the measured density and shear wave velocity (i.e., $\mu = \rho v^2$), and the determined shear modulus may be compared to the threshold shear modulus vale. In one example, the threshold shear modulus value may be approximately 200 kPa. If the shear modulus of the biological tissue sample exceeds 200 kPa, a determination can be made that fixation of the biological tissue sample is complete. The method may then continue with providing the liquid dye to the biological tissue sample.

Figure 6:
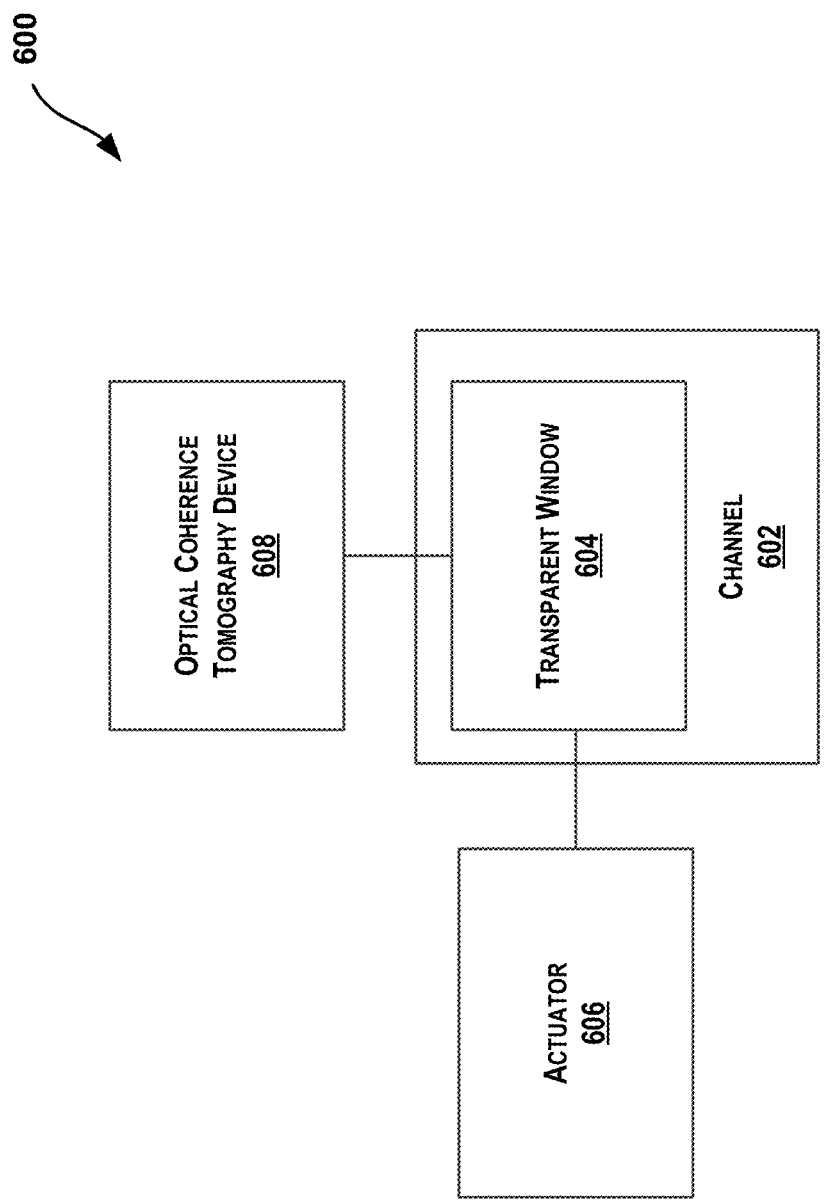
FIG. 6 illustrates a simplified block diagram of a fluidic device, according to an example embodiment.

FIG. 6 illustrates an example fluidic device 600. The fluidic device 600 may include a channel 602 including a transparent window 604. The channel 602 may be configured to receive a biological tissue sample. Further, one end of the channel 602 may be open to the environment. The channel 602 must be sized to accommodate the clinical range of tissue biopsies (e.g., L=0.5-2.0 cm, D=0.3-1.5 mm). Further, the volume of the channel may between about 0.3 μL and about 40 μL. The channel 602 may include a soft substrate, such as PDMS, which is optically translucent and may be fabricated in a fashion to produce a thin, pliable transparent window 604 for optical and/or acoustic monitoring. The transparent window 604 may have a thickness between about 0.1 mm and about 1 mm.

The fluidic device 600 may further include an actuator 606 configured to provide shear waves to the biological tissue sample positioned in the channel 602. As discussed above, the actuator 606 may comprise a piezoelectric actuator that contacts the biological tissue sample to provide the shear waves to the biological tissue sample. The piezoelectric actuator may be placed preferentially in a more vertical position to produce transverse oscillations in the biological tissue sample. In one example, more than one actuator may be used to provide shear waves to the biological tissue sample. Further, the fluidic device 600 may include an optical coherence tomography device 608 positioned adjacent to the transparent window 604. The optical coherence tomography device 608 is configured to measure a shear wave speed within the biological tissue sample.

Figure 7:
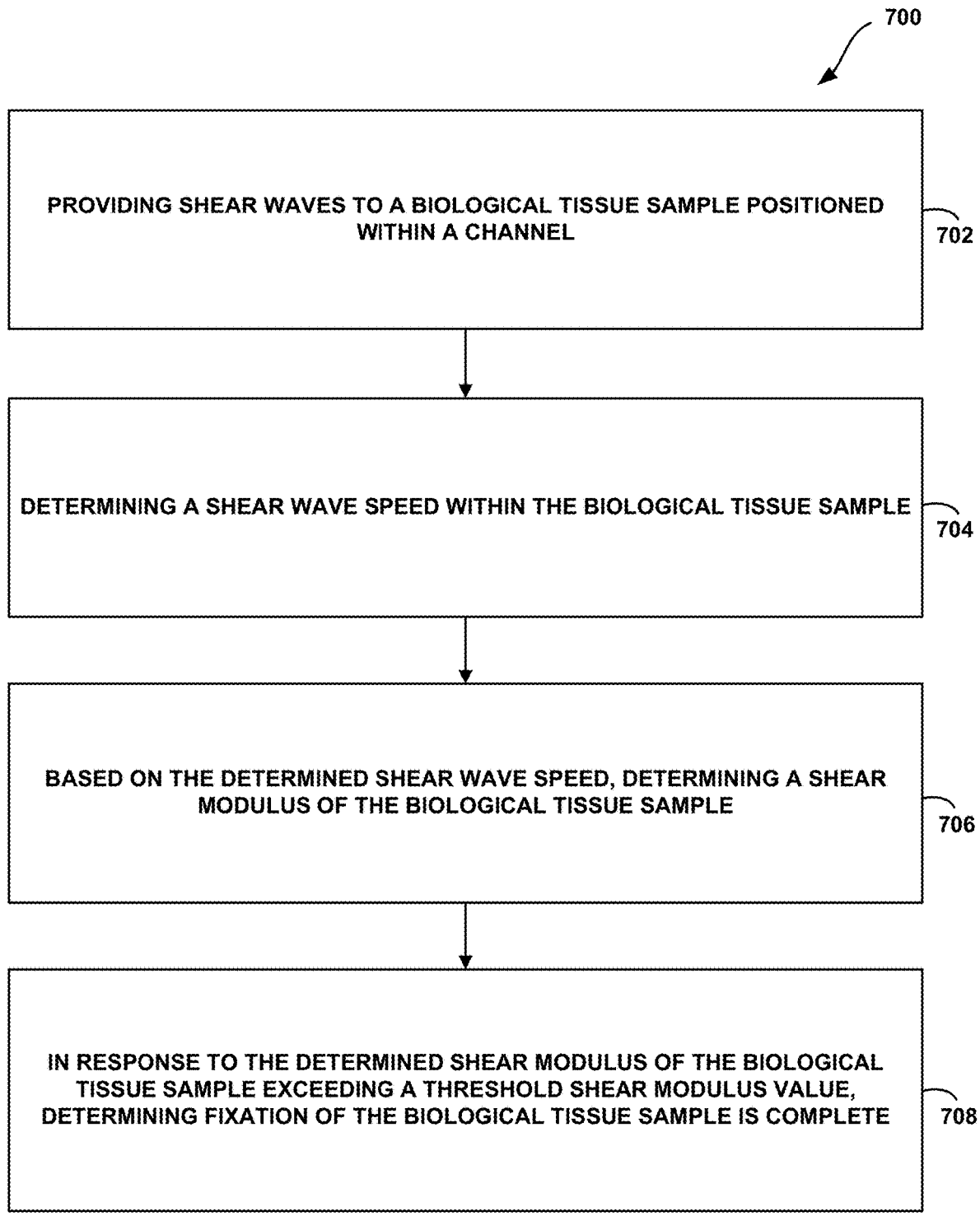
FIG. 7 is a flowchart illustrating an example method according to an example embodiment.

FIG. 7 is a block diagram of an example method for detecting fixation of a biological tissue sample. Method 700 shown in FIG. 7 presents an embodiment of a method that could be used by the fluidic devices described in FIG. 6, as an example. Method 700 may include one or more operations, functions, or actions as illustrated by one or more of blocks 702-708. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

Initially, at block 702, the method 700 includes providing shear waves to a biological tissue sample positioned within a channel. As described above, the fluidic device may an actuator configured to provide shear waves to the biological tissue sample positioned in the channel.

Next, at block 704, the method 700 includes determining a shear wave speed within the biological tissue sample. As described above, the fluidic device may further include an optical coherence tomography device configured to measure shear wave speed within the biological tissue. The top surface of the curved channel may include a flexible window comprising a thin (<0.2 mm), flexible PDMS membrane in order to ascertain if OCT imaging, or propagating shear wave was significantly impacted by the substrate. In one particular example, the shear wave propagation may be tracked at a frame rate of 44.8 kHz using a phase-sensitive optical coherence tomography device. The local propagation speed of the shear wave may be calculated at each pixel of the imaging plane. The shear wave speed (v) is known to be related to soft tissue stiffness (i.e., $E\sim 3\mu=3\rho v^2$, where E=Young's modulus, $\mu$=shear modulus and $\rho$=density).

Next, at block 706, the method 700 includes, based on the determined shear wave speed, determining a shear modulus of the biological tissue sample. In particular, the shear modulus ($\mu$) may be calculated based on the measured density and shear wave velocity (i.e., $\mu=\rho v^2$), and the determined shear modulus may be compared to the threshold shear modulus vale. In one example, the threshold shear modulus value may be approximately 200 kPa.

Finally, at block 708, the method 700 includes, in response to the determined shear modulus of the biological tissue sample exceeding a threshold shear modulus value, determining fixation of the biological tissue sample is complete. Fixation makes tissue tougher and more stiff, hence the shear wave traverses the tissue biopsy at a different velocity than unfixed tissue. Shear waves travel approximately four times faster through fixed tissue than unfixed tissue which translates to a shear modulus of 227 and 18 kPa for fixed and unfixed pancreatic tissue, respectively.

Figure 8:
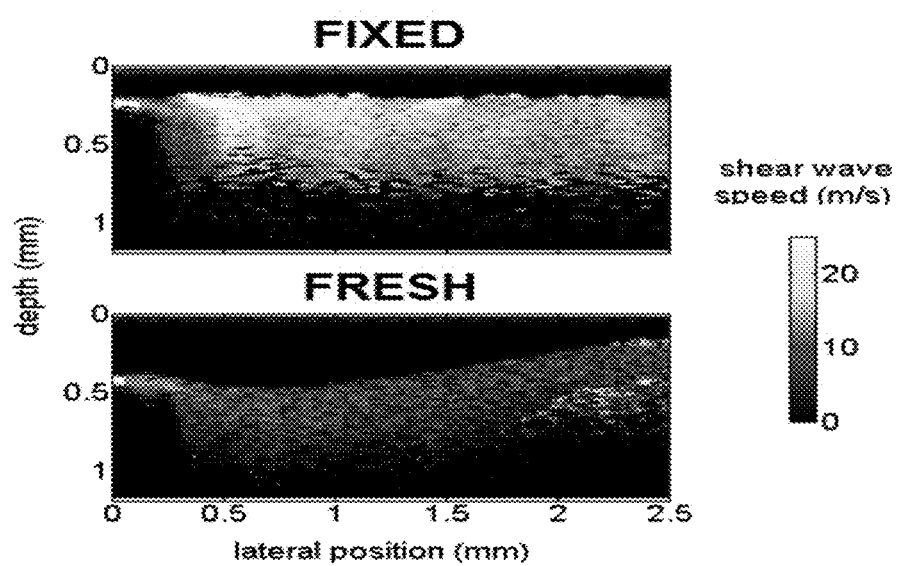
FIG. 8 illustrates shear wave velocity distribution in a fixed and fresh biological tissue ample, according to an example embodiment.

FIG. 8 illustrates shear wave velocity distribution in fixed and fresh pancreas samples. Fixed samples are more elastic in comparison to fresh ones since a distinct shear wave map was able to be visualized across the fixed specimen. The source of actuation is located at the top left corner in both images.

In certain embodiments, such as shown in any one of FIGS. 1-4, and 6, example fluidic devices may be made using an additive-manufacturing process, such as stereolithography. As such, the example fluidic devices described above may include a variety of materials, including calcium carbonate of poly(dimethylsiloxane) (PDMS), as examples.

In one example, the additive-manufacturing process is a multi-material additive-manufacturing process such that various components of the fluidic device may be formed using a material with a greater elasticity than the other components. For example, the curved channels may be created with a material having greater elasticity than the input interface and output interface of the fluidic device. Other examples are possible as well.

Each of the fluidic devices described in FIGS. 1-4, and 6 may represent a module, a segment, or a portion of program code, which includes one or more instructions executable by a processor or computing device for creating such devices using an additive-manufacturing system. The program code may be stored on any type of computer readable medium, for example, such as a storage device including a disk or hard drive. The computer readable medium may include non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device.

Figure 9:
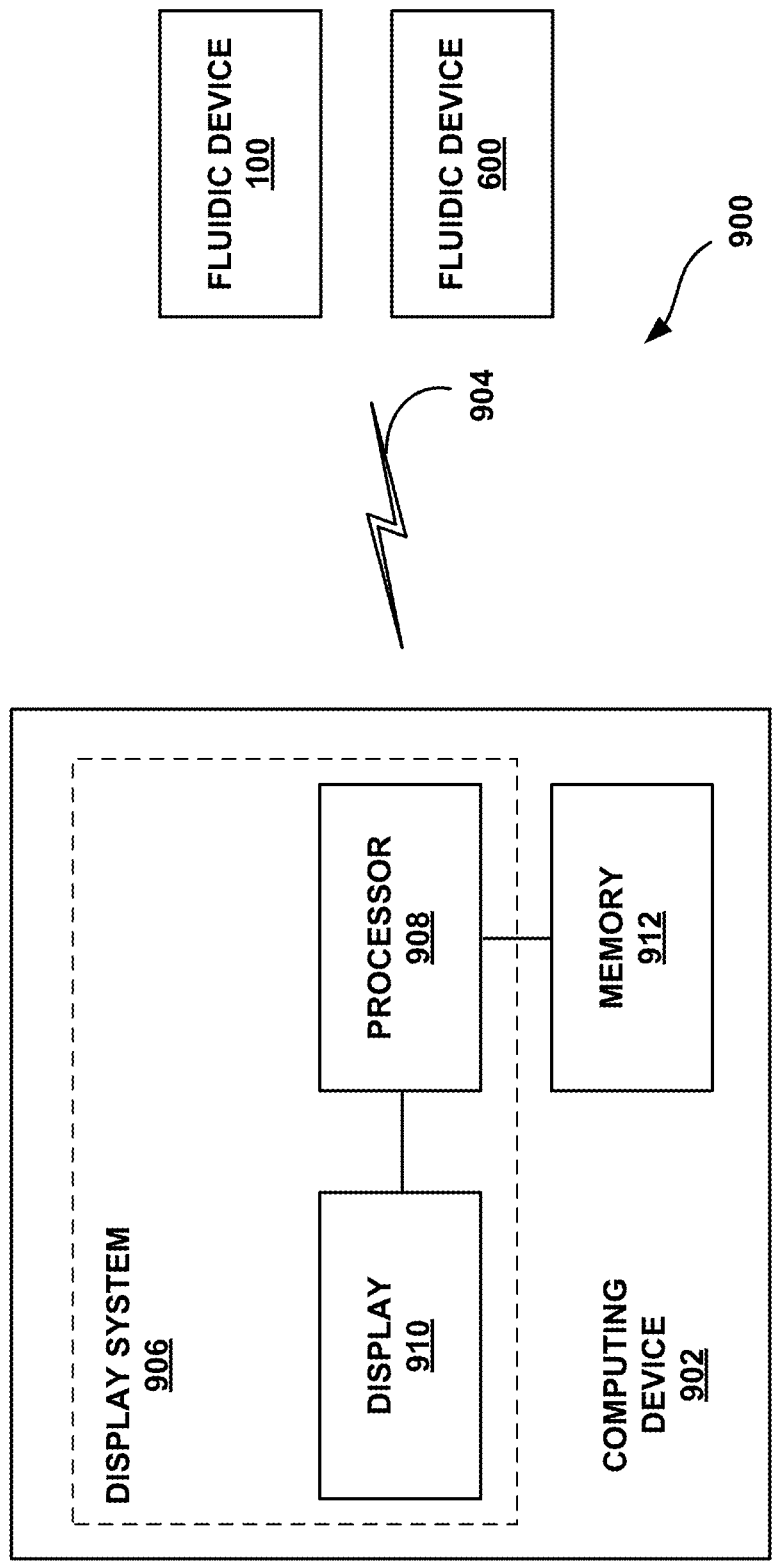
FIG. 9 illustrates a schematic drawing of a computer network infrastructure, according to an example embodiment.

FIG. 9 illustrates an example schematic drawing of a computer network infrastructure. In one system 900, a computing device 902 communicates with the fluidic device 100 and/or the fluidic device 600 using a communication link 904, such as a wired or wireless connection. The computing device 902 may be any type of device that can receive data and display information corresponding to or associated with the data. For example, the computing device 902 may be a mobile phone, a tablet, or a personal computer as examples.

Thus, the computing device 902 may include a display system 906 comprising a processor 908 and a display 910. The display 910 may be, for example, an optical see-through display, an optical see-around display, or a video see-through display. The processor 908 may receive data from the fluidic device 100 and/or the fluidic device 600, and configure the data for display on the display 910. Depending on the desired configuration, processor 908 can be any type of processor including, but not limited to, a microprocessor, a microcontroller, a digital signal processor, or any combination thereof.

The computing device 902 may further include on-board data storage, such as memory 912 coupled to the processor 908. The memory 912 may store software that can be accessed and executed by the processor 908, for example. Further, processor 908 may receive data from the fluidic device 100 and/or the fluidic device 600, and configure the data for storage in the memory 912. The memory 912 can include any type of memory now known or later developed including but not limited to volatile memory (such as RAM), non-volatile memory (such as ROM, flash memory, etc.) or any combination thereof.

According to an example embodiment, the computing device 902 may include program instructions that are stored in the memory 912 (and/or possibly in another data-storage medium) and executable by the processor 908 to facilitate the various functions described herein. Although various components of the system 900 are shown as distributed components, it should be understood that any of such components may be physically integrated and/or distributed according to the desired configuration of the computing system.

The fluidic device 100 and/or the fluidic device 600 and the computing device 900 may contain hardware to enable the communication link 904, such as processors, transmitters, receivers, antennas, etc.

In FIG. 9, the communication link 904 is illustrated as a wireless connection; however, wired connections may also be used. For example, the communication link 904 may be a wired link via a serial bus such as a universal serial bus or a parallel bus. A wired connection may be a proprietary connection as well. The communication link 904 may also be a wireless connection using, e.g., Bluetooth® radio technology, communication protocols described in IEEE 802.11 (including any IEEE 802.11 revisions), Cellular technology (such as GSM, CDMA, UMTS, EV-DO, WiMAX, or LTE), or Zigbee® technology, among other possibilities.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. Further, many of the elements that are described are functional entities that may be implemented as discrete or distributed components or in conjunction with other components, in any suitable combination and location, or other structural elements described as independent structures may be combined.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

Since many modifications, variations, and changes in detail can be made to the described example, it is intended that all matters in the preceding description and shown in the accompanying figures be interpreted as illustrative and not in a limiting sense. Further, it is intended to be understood that the following clauses (and any combination of the clauses) further describe aspects of the present description.

We claim:

1. A fluidic device comprising:
   one or more curved channels each having a channel input and a channel output, wherein the one or more curved channels each have a substantially circular cross-section, wherein the one or more curved channels include at least a first segment between the channel input and the channel output, a second segment between the first segment and the channel output, and a third segment between the second segment and the channel output, and wherein the first segment has a first diameter that is different than a second diameter of the second segment, and wherein the third segment has a third diameter that is different than the second diameter;
   an input interface directly coupling the channel input of the one or more curved channels to an exterior of the fluidic device, wherein the input interface is configured to receive a biological tissue sample having a diameter that is about 10% to about 20% less than the diameter of the one or more curved channels, and wherein the input interface comprises a septum that provides a fluid-tight seal between the exterior of the fluidic device and the one or more curved channels; and
   an output interface directly coupling the channel output of the one or more curved channels to the exterior of the fluidic device, wherein an entire length of each of the one or more curved channels from the input interface to the output interface has a diameter greater than 0.2 mm and up to 5 mm.

2. The fluidic device of claim 1, wherein the input interface is positioned at a first height, wherein the output interface is positioned at a second height, and wherein the first height is different than the second height such that the one or more curved channels extends from one plane to another.

3. The fluidic device of claim 1, wherein the one or more curved channels have a radius of curvature between about 0.5 cm and about 10 cm.

4. The fluidic device of claim 1, further comprising:
   a first reservoir in fluid communication with the one or more curved channels, wherein the first reservoir includes an aqueous liquid; and
   a second reservoir in fluid communication with the one or more curved channels, wherein the second reservoir includes a liquid dye.

5. The fluidic device of claim 4, further comprising:
   a third reservoir in fluid communication with the one or more curved channels, wherein the third reservoir includes a liquid fixative; and
   a fourth reservoir in fluid communication with the one or more curved channels, wherein the third reservoir includes a liquid optical clearing agent.

6. The fluidic device of claim 5, further comprising one or more pumps in fluid communication with one or more of the first reservoir, the second reservoir, the third reservoir, and the fourth reservoir.

7. The fluidic device of claim 1, wherein the one or more curved channels include a flexible window with a thickness between about 0.1 mm to about 1 mm.

8. The fluidic device of claim 7, further comprising:
   an imaging device positioned adjacent to the flexible window, wherein the imaging device is configured to measure a transparency of the biological tissue sample and/or an intensity profile of the biological tissue sample.

9. The fluidic device of claim 1, further comprising:
   at least one processor; and
   data storage including program instructions stored thereon that when executed by the at least one processor, cause the fluidic device to:
      provide a liquid dye to the one or more curved channels to contact the biological tissue sample, wherein a flow rate of the liquid dye through the one or more curved channels is less than a threshold flow rate, and wherein the biological tissue sample is substantially stationary when the flow rate is less than the threshold flow rate; and
      provide an aqueous liquid to the one or more curved channels to contact the biological tissue sample, wherein a flow rate of the aqueous liquid through the one or more curved channels is greater than the threshold flow rate, and wherein the biological tissue sample passes through the one or more curved channels to the output interface of the fluidic device when the flow rate is greater than the threshold flow rate.

10. The fluidic device of claim 9, wherein the program instructions are further executable by the at least one processor to cause the fluidic device to:
provide a liquid fixative to the one or more curved channels to contact the biological tissue sample, wherein a flow rate of the liquid fixative through the one or more curved channels is less than the threshold flow rate such that the biological tissue sample is substantially stationary; and
provide a liquid optical clearing agent to the one or more curved channels to contact the biological tissue sample, wherein a flow rate of the liquid optical clearing agent through the one or more curved channels is less than the threshold flow rate such that the biological tissue sample is substantially stationary.

11. The fluidic device of claim 10, wherein the program instructions are further executable by the at least one processor to cause the fluidic device to:
measure, via an imaging device, a first transparency of the biological tissue sample prior to providing the optical clearing agent to the one or more curved channels;
measure, via the imaging device, a second transparency of the biological tissue after providing the optical clearing agent to the one or more curved channels; and
in response to the second transparency exceeding the first transparency by at least five times, provide the aqueous liquid to the one or more curved channels to contact the biological tissue sample.

12. The fluidic device of claim 10, wherein the program instructions are further executable by the at least one processor to cause the fluidic device to:
measure, via an imaging device, an intensity profile of the biological tissue sample after providing the optical clearing agent to the one or more curved channels;
if the intensity profile exceeds a threshold intensity profile value, then pass the biological tissue sample through the one or more curved channels via the aqueous liquid to a three-dimensional imaging device; and
if the intensity profile does not exceed the threshold intensity profile value, then pass the biological tissue sample through the one or more curved channels via the aqueous liquid to a two-dimensional imaging device.

13. The fluidic device of claim 1, further comprising:
an actuator configured to provide shear waves to the biological tissue sample; and
an optical coherence tomography device configured to measure a shear wave speed within the biological tissue sample.

14. The fluidic device of claim 1, wherein the septum comprises a one-way septum, and wherein the one-way septum is configured to receive an entire coring needle to thereby deposit the biological tissue sample into the one or more curved channels.

15. The fluidic device of claim 1, wherein the output interface provides a fluid-tight seal between the exterior of the fluidic device and the one or more curved channels.

16. The fluidic device of claim 1, wherein the one or more curved channels are positioned completely within an interior of the fluidic device.

17. The fluidic device of claim 1, wherein the septum comprises a puckered septum, and wherein a coring needle is configured to be press fit into the puckered septum such that an entirety of the coring needle is positioned within the input interface to thereby deposit the biological tissue sample into the one or more curved channels.

* * * * *